(12) United States Patent
Izumori et al.

(10) Patent No.: US 7,691,619 B2
(45) Date of Patent: Apr. 6, 2010

(54) SEQUENCE OF THERMOTOLERANT L-RHAMNOSE ISOMERASE GENE AND USE OF THE SAME

(75) Inventors: Ken Izumori, Kagawa (JP); Goro Takata, Kagawa (JP); Masaaki Tokuda, Kagawa (JP)

(73) Assignee: Rare Sugar Production Technical Research Laboratories, LLC, Kagawa (JP)

( * ) Notice: Subject to any disclaimer, the term of this patent is extended or adjusted under 35 U.S.C. 154(b) by 110 days.

(21) Appl. No.: 11/660,959

(22) PCT Filed: Aug. 23, 2005

(86) PCT No.: PCT/JP2005/015236

§ 371 (c)(1),
(2), (4) Date: Sep. 28, 2007

(87) PCT Pub. No.: WO2006/022239

PCT Pub. Date: Mar. 2, 2006

(65) Prior Publication Data

US 2009/0004694 A1 Jan. 1, 2009

(30) Foreign Application Priority Data

Aug. 24, 2004 (JP) .............................. 2004-244253
Mar. 29, 2005 (JP) .............................. 2005-095538

(51) Int. Cl.
*C12N 9/90* (2006.01)
*C12P 19/24* (2006.01)
*C12P 19/02* (2006.01)
*C12P 21/04* (2006.01)
*C07H 21/04* (2006.01)

(52) U.S. Cl. .................... 435/233; 435/94; 435/105; 435/69.7; 536/23.2; 536/23.7

(58) Field of Classification Search .................. None
See application file for complete search history.

(56) References Cited

FOREIGN PATENT DOCUMENTS

JP 2005-102503 A 4/2005

WO WO 2004/063369 A1 7/2004

OTHER PUBLICATIONS

Broun et al., Catalytic plasticity of fatty acid modification enzymes underlying chemical diversity of plant lipids. Science, 1998, vol. 282: 1315-1317.*
Seffernick et al., Melamine deaminase and Atrazine chlorohydrolase: 98 percent identical but functionally different. J. Bacteriol.,2001, vol. 183 (8): 2405-2410.*
Witkowski et al., Conversion of b-ketoacyl synthase to a Malonyl Decarboxylase by replacement of the active cysteine with glutamine. Biochemistry, 1999, vol. 38: 11643-11650.*
Kunst et al., The complete genome sequence of the gram-positive bacterium *Bacillus subtilis*. Nature, vol. 390: 249-256 and supplemental table.*
Takami et al., Complete genome sequence of the alkaliphilic bacterium *Bacillus halodurans* and genomic sequence comparison with *Bacillus subtilis*. Nucleic Acids Res., 2000, vol. 28 (21): 4317-4331.*
B. Oudega et al.; Analysis of the *Bacillus subtilis* genome: cloning and nucleotide sequence of a 62 kb region between 275 degree (rrnB) and 284 degrees (pai), Microbiology 1997, vol. 143, No. 8, pp. 2769 to 2774. (Cited in the international search report).
L-rhamnose isomerase [*Bacillus halodurans* C-125] Jul. 14, 2004 [online]; National Center for Biotechnology Information [retrieved on Nov. 10, 2005] Retrieved from: Entrez Protein, Accession No. BAB05271. (Cited in the international search report), Jul. 13, 2004.
Hiromi Okada et al.; "*Bacillus stearothermophilus* Yurai no L-rhamnose insomerase to sono idenshi no Cloning", Japan Society for Bioscience, Biotechnology, and Agrochemistry Taikai Koen Yoshishu, Mar. 5, 2005, vol. 2005, p. 203, 30D075α (Cited in the international search report).
S. H. Bhuiyan et al.; "D-allose production from D-psicose using immobilized L-rhamnose isomerase", J. Ferment.Bioeng, 1998, vol. 85, No. 5, pp. 539 to 541. (Cited in the international search report).
International Search Report of PCT/JP2005/015236, date of mailing Nov. 29, 2005, Feb. 23, 2007.

* cited by examiner

*Primary Examiner*—Ganapathirama Raghu
(74) *Attorney, Agent, or Firm*—Westerman, Hattori, Daniels & Adrian, LLP

(57) ABSTRACT

The invention relates to an isolated protein including an amino acid sequence represented by SEQ ID NO:2 and having an L-rhamnose isomerase activity. This novel enzyme has a higher reaction efficiency between D-psicose and D-allose and is excellent in thermal stability.

5 Claims, 8 Drawing Sheets

[Fig.1A]
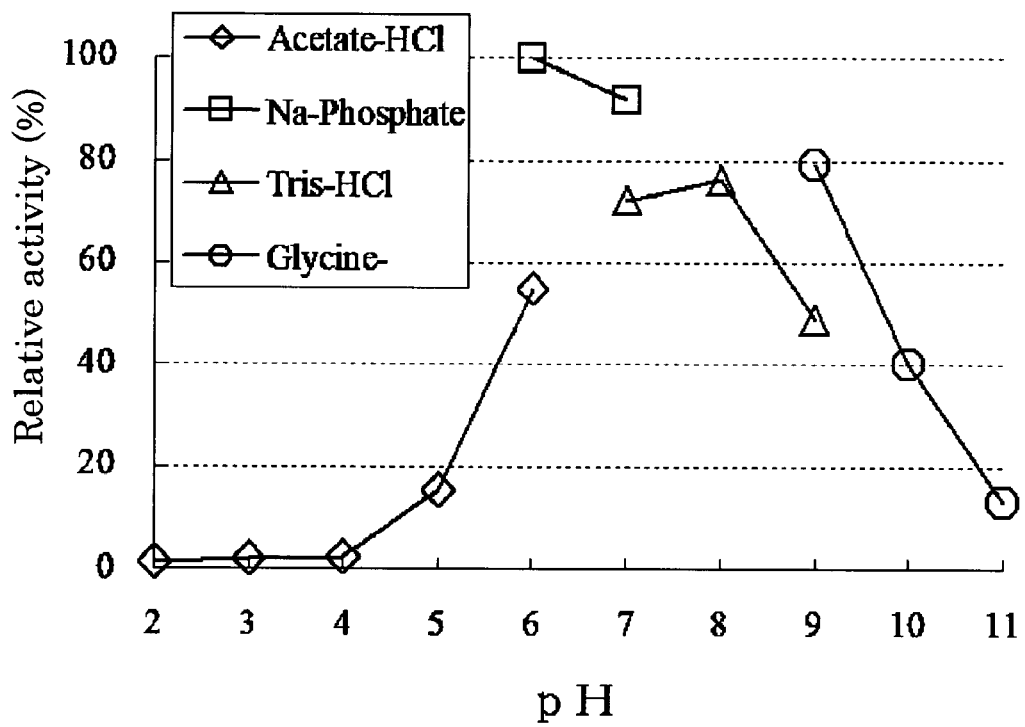
[Fig.1B]
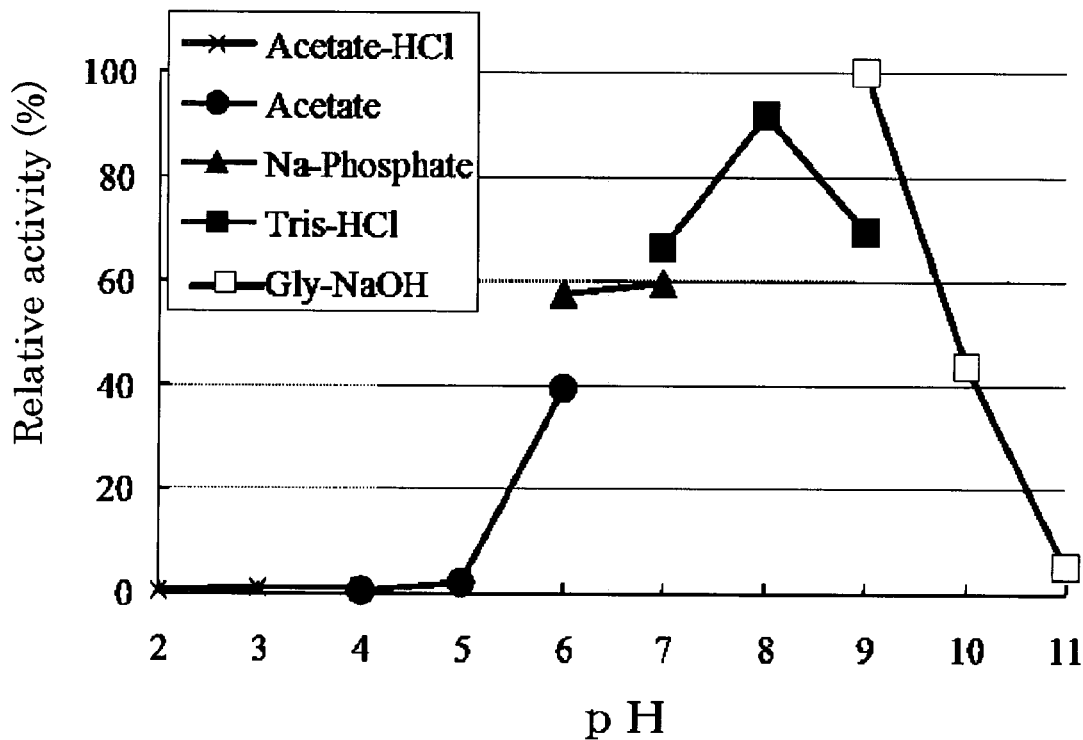

[Fig. 2A]
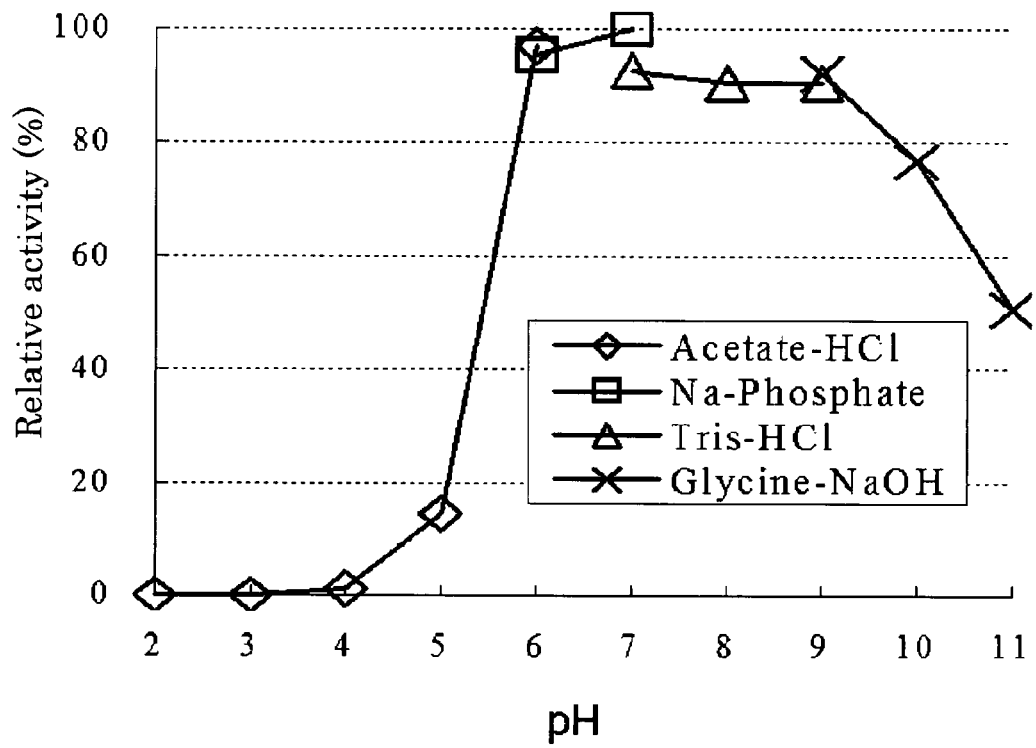
[Fig. 2B]
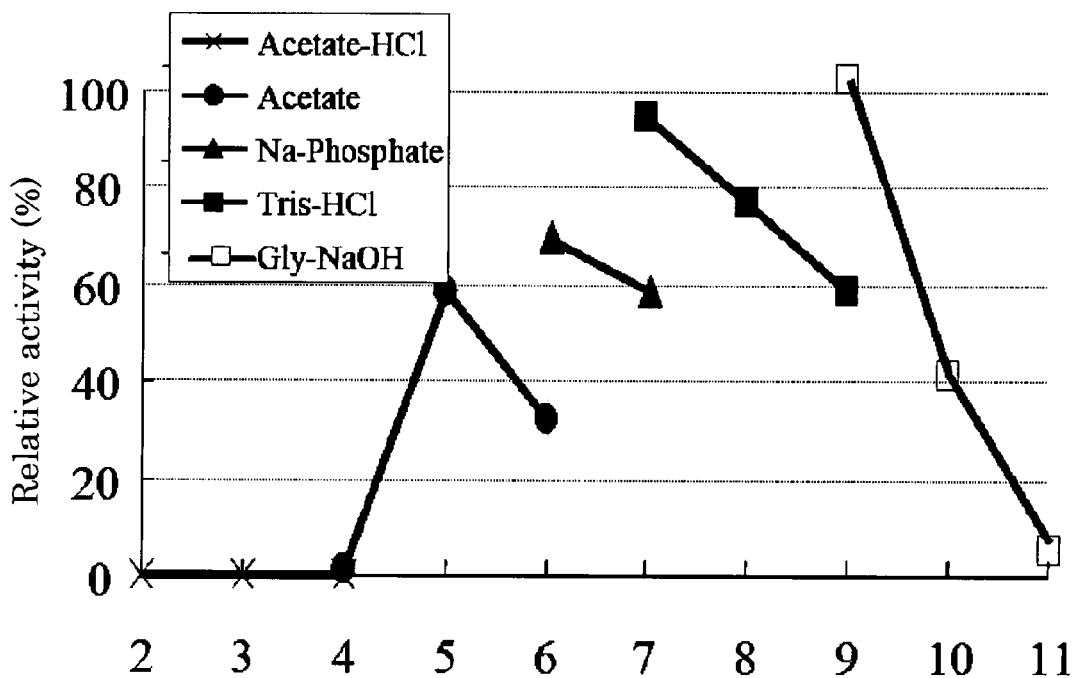

[Fig.3A]
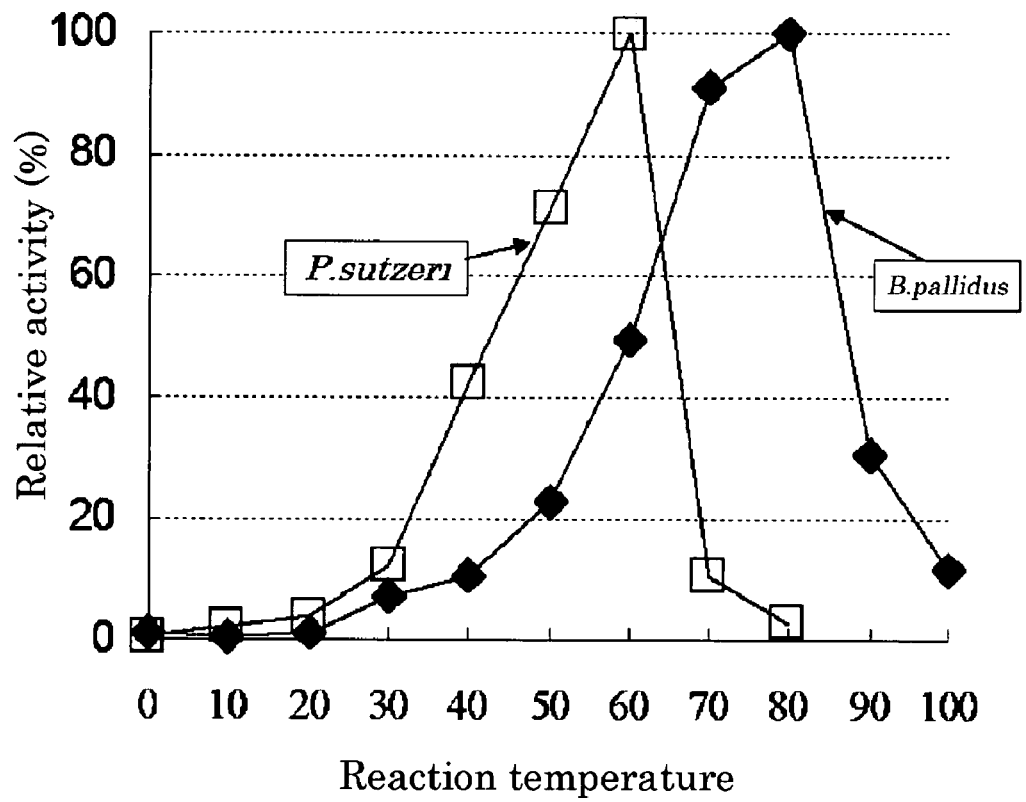
[Fig.3B]
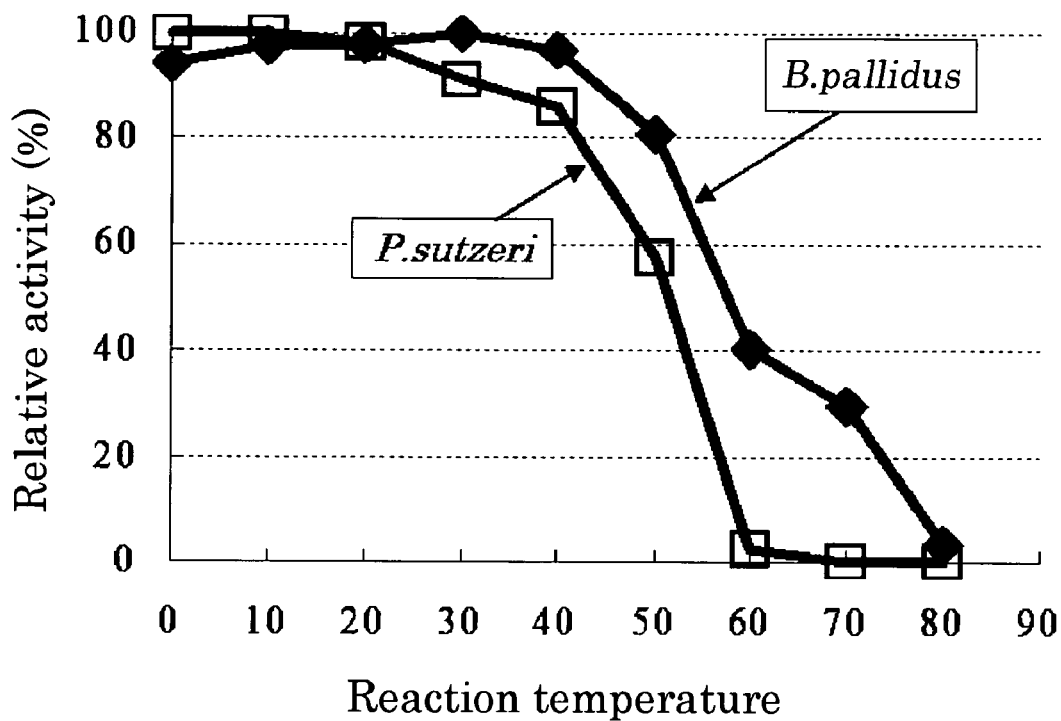

[Fig.4]

```
  1  ATGGCTGAATTCAGGATCGCTCAGGATGTCGTTGCGCGGGAAAACGACAGGCGCGCCTCG    60
  1   M  A  E  F  R  I  A  Q  D  V  V  A  R  E  N  D  R  R  A  S    20
 61  GCGCTGAAGGAAGACTACGAGGCGCTCGGCGCGAATCTCGCCCGCCGTGGCGTCGACATC   120
 21   A  L  K  E  D  Y  E  A  L  G  A  N  L  A  R  R  G  V  D  I    40
121  GAGGCCGTCACGGCCAAGGTCGAAAAGTTCTTCGTCGCCGTCCCCTCCTGGGGCGTCGGC   180
 41   E  A  V  T  A  K  V  E  K  F  F  V  A  V  P  S  W  G  V  G    60
181  ACGGGCGGCACGCGCTTTGCGCGCTTCCCCGGCACCGGCGAGCCGCGCGGCATCTTCGAC   240
 61   T  G  G  T  R  F  A  R  F  P  G  T  G  E  P  R  G  I  F  D    80
241  AAGCTGGACGACTGCGCCGTCATCCAGCAGCTGACACGCGCCACGCCCAATGTCTCGCTG   300
 81   K  L  D  D  C  A  V  I  Q  Q  L  T  R  A  T  P  N  V  S  L   100
301  CATATTCCGTGGGACAAGGCCGATCCGAAGGAGCTGAAGGCCAGGGGCGACGCCCTCGGC   360
101   H  I  P  W  D  K  A  D  P  K  E  L  K  A  R  G  D  A  L  G   120
361  CTCGGCTTCGACGCGATGAACTCCAATACCTTCTCCGATGCGCCCGGCCAGGCGCATTCC   420
121   L  G  F  D  A  M  N  S  N  T  F  S  D  A  P  G  Q  A  H  S   140
421  TACAAATACGGCTCGCTCAGCCACACGGATGCGGCAACGCGCGCCCAGGCGGTCGAGCAC   480
141   Y  K  Y  G  S  L  S  H  T  D  A  A  T  R  A  Q  A  V  E  H   160
481  AATCTGGAATGCATCGAGATCGGCAAGGCCATCGGCTCCAAGGCGCTGACGGTCTGGATC   540
161   N  L  E  C  I  E  I  G  K  A  I  G  S  K  A  L  T  V  W  I   180
541  GGTGACGGCTCCAACTTCCCCGGCCAGAGTAACTTCACCAGGGCTTTCGAACGTTATCTC   600
181   G  D  G  S  N  F  P  G  Q  S  N  F  T  R  A  F  E  R  Y  L   200
601  TCGGCGATGGCGGAGATCTACAAGGGCCTGCCGGATGACTGGAAGCTGTTCTCCGAGCAC   660
201   S  A  M  A  E  I  Y  K  G  L  P  D  D  W  K  L  F  S  E  H   220
661  AAGATGTACGAGCCGGCCTTCTATTCGACCGTCGTGCAGGACTGGGGCACGAATTATCTC   720
221   K  M  Y  E  P  A  F  Y  S  T  V  V  Q  D  W  G  T  N  Y  L   240
721  ATCGCCCAGACGCTCGGCCCCAAGGCCCAGTGCCTCGTCGATCTCGGCCATCACGCGCCG   780
241   I  A  Q  T  L  G  P  K  A  Q  C  L  V  D  L  G  H  H  A  P   260
781  AACACCAATATCGAGATGATCGTCGCCCGGCTCATCCAGTTCGGCAAGCTCGGCGGCTTC   840
261   N  T  N  I  E  M  I  V  A  R  L  I  Q  F  G  K  L  G  G  F   280
841  CATTTCAACGATTCCAAATACGGCGACGACGACCTCGATGCCGGCGCCATCGAGCCCTAT   900
281   H  F  N  D  S  K  Y  G  D  D  D  L  D  A  G  A  I  E  P  Y   300
901  CGCCTCTTCCTCGTCTTCAACGAGCTGGTGGATGCGGAGGCGCGCGGCGTCAAGGGCTTC   960
301   R  L  F  L  V  F  N  E  L  V  D  A  E  A  R  G  V  K  G  F   320
961  CACCCGGCCCACATGATCGACCAGTCGCACAACGTCACCGACCCGATCGAGAGCCTGATC  1020
321   H  P  A  H  M  I  D  Q  S  H  N  V  T  D  P  I  E  S  L  I   340
1021 AACAGCGCGAACGAAATCCGTCGCGCCTATGCGCAGGCCCTCCTTGTCGACCGCGCGGCG  1080
341   N  S  A  N  E  I  R  R  A  Y  A  Q  A  L  L  V  D  R  A  A   360
1081 CTTTCCGGCTACCAGGAGGACAACGACGCCCTGATGGCGACGGAAACGTTGAAGCGCGCC  1140
361   L  S  G  Y  Q  E  D  N  D  A  L  M  A  T  E  T  L  K  R  A   380
1141 TACCGTACCGATGTGGAGCCGATCCTCGCCGAGGCCCGCCGCCGCACGGGCGGCGCCGTC  1200
381   Y  R  T  D  V  E  P  I  L  A  E  A  R  R  R  T  G  G  A  V   400
1201 GACCCCGTCGCGACCTATCGGGCCAGCGGCTACCGCGCCAGGGTCGCCGCCGAGCGCCCC  1260
401   D  P  V  A  T  Y  R  A  S  G  Y  R  A  R  V  A  A  E  R  P   420
1261 GCCTCCGTCGCGGGTGGCGGCGGCATCATCTGA  1293
421   A  S  V  A  G  G  G  G  I  I  *   431
```

[Fig.5]

```
M---AEFRIAQDVVARENDRRASALKEDYEALGANLARRGVDIEAVTAKVEKFFVA--VP    55
MTIKANYDSAKQAYEKWGIDVEEALRQLEQVPISIHCWQGDDIEGFEVNKGELSGGIDVT    60

SWGVGTGGTRFARFPGTGEPRGIFDKLDDCAVIQQLTRATPNVSLHIPWDKADPKELKAR   115
GNYPGKAQTPEELRRDLEKALSLIPGKHRVNLHAIYAETNREAVERDELKPQHFENWVKW   120

GDALGLGFDAMNSNTFSDAPGQAHSYKYGSLSHTDAATRAQAVEHNLEGIEIGKAIGSKA   175
AKNLGLGLDFNPTLFSHEKAADGLT-----LSHPDPDIREFWIRHCIACRRIGEYFGKEL   175

LTVWIGDGSNFPGQSNFTR----AFERYLSAMAEIY-KGLPDDWKLFS-EHKMYEPAFYS   229
GTPCLTNIWIPDGYKDIPSDRLTPRKRLKESLDRIFSEEISEQHNLDSIESKLFGLGSES   235

TVVQDWGTNYLIAQTLGPKAQCLVDLGH-HAPNTNIEMIVARLIQFGKLGGFHFNDSKYG   288
YVV--GSHEFYLAYALTNHKLCLLDTGHFHPTETVSNKISSMLLYTDKLA-LHVSRPVRW   292

DDDLDAGAIEPYRLFLVFNELVDAEARGVKGFHPAHMIDQSHNVTDPIESLINSANEIRR   348
DSDHVVVLDDELR------EIALEIVRNHALEKVAIGLDFFDASINRVAAWTIGTRNMIK   346

AYAQALLVDRAALSGYGEDNDALMATETLKRAYRTDVEPILAEARRRTGGAVDPVATYRA   408
ALLYALLLPNGYLKQLQEEGRYTERLALMEEFKTYPFGAIWDSYCEQMGVPVKEAWLYDI   406

SGYRARVAAERPASVAGGGGII    430
KEYEQQVLLKRKASSP----IV    424
```

Upper: *Pseudomonas stutzeri*
Lower: *Bacillus subtilis*

[Fig.6]

```
Rhl    MAEFRIAQDVVARENDRRASALKEDYEALGANLARRGVDIEAVTAKVEKFFVAVPSWGVG    60
SISTR  MTE---------------------------------LAAVKAALKTQAVETPSWAYG     24
SITHE  MI----------------------------------NMERIFKELDELKFELPSWAFS    24

Rhl    TGGTRFARFPGTGEPRGIFDKLDDCAVIQQLTRATPNVSLHIPWDKA-DPKELKARGDAL  119
SISTR  NSGTRFKVFAQPGVPRDPFEKLDDAAKVHEFTGAAPTVALHIPWDRVEDYAALAAHAEKR   84
SITHE  DAGTRFAVFHEEGAARNVFERIEDAALVHRLTGCCPSVALHIPWDKVENWEELREFAEEK   84

Rhl    GLGFDAMNSNTFSDAPGQAHSYKYGSLSHTDAATRAQAVEHNLECIEIGKAIGSKALTVW  179
SISTR  GVRIGAINSNTFQDD----DYRLGSICHPDAAVRRKAVDHLLECVDIMDATGSRDLKLW  139
SITHE  GLKIGAINPNLFQDP----DYKYGSLTNPSEKIRKKAIAHVMECVDIAEKTGSKVISLW  139

Rhl    IGDGSNFPGQSNFTRAFERYLSAMAEIYKGLPDDWKLFSEHKMYEPAFYSTVVQDWGTNY  239
SISTR  FADGTNYPGQDDIRSRQDRLAEGLAEVYERLGEGGQRMLLEYKLFEPAFYTTDVPDWGTAY  199
SITHE  LADGTDYPGQDDFRSRKKRLEESLRYIYENMPADMYLLIEYKFFEPAFYHTDIPDWGMSY  199

Rhl    LIAQTLGPKAQCLVDLGHHAPNTNIEMIVARLIQFGKLGGFHFNDSKYGDDDLDAGAIEP  299
SISTR  AHCLKLGEKAQVVVDTGHHAPGTNIEFIVATLLREGKLGGFDFNSRFYADDDLMVGAADP  259
SITHE  LLSEKLGERALVLVDLGHHPQGTNIEYIVATLLSEKKLGGFHLNNRKYADDDLTIASINP  259

Rhl    YRLFLVFNELVDAEARGVKGFH---PAHMIDQSHNVTDPIESLINSANEIRRAYAQALLV  356
SISTR  FQLFRI--MYEVVRGGGFTSD---VAFMLDQCHNIEAKIPAIIRSVMNVQEATAKALLV  313
SITHE  YEVFLIFKEIVFAKRDPELSDSAKKVVLMFDQAHITKPKILAMIQSVLIAQELFTKALLI  319

Rhl    DRAALSGYQEDNDALMATETLKRAYRTDVEPILAEARRRTGGAVDPVATYRASGYRARVA  416
SISTR  DGTALAEAQAAGDVLEANAVLMDAYNTDVRPLLREVREESGLDPEPMKAYRSCGWAEKVV  373
SITHE  DENRLREAQKNYDVVEAEEILLDAFRTDVRPILREYRRQKGLPEDPLRVFREEDYMEKRR  379

Rhl    AERPASVAGGGGII    430
SISTR  AERIGGQQAGWG-A   386
SITHE  RERR---------    383
```

| | Identity |
|---|---|
| *Streptomyces coelicolor* | 45% |
| *Thermotoga maritima* | 39% |

[Fig.7]
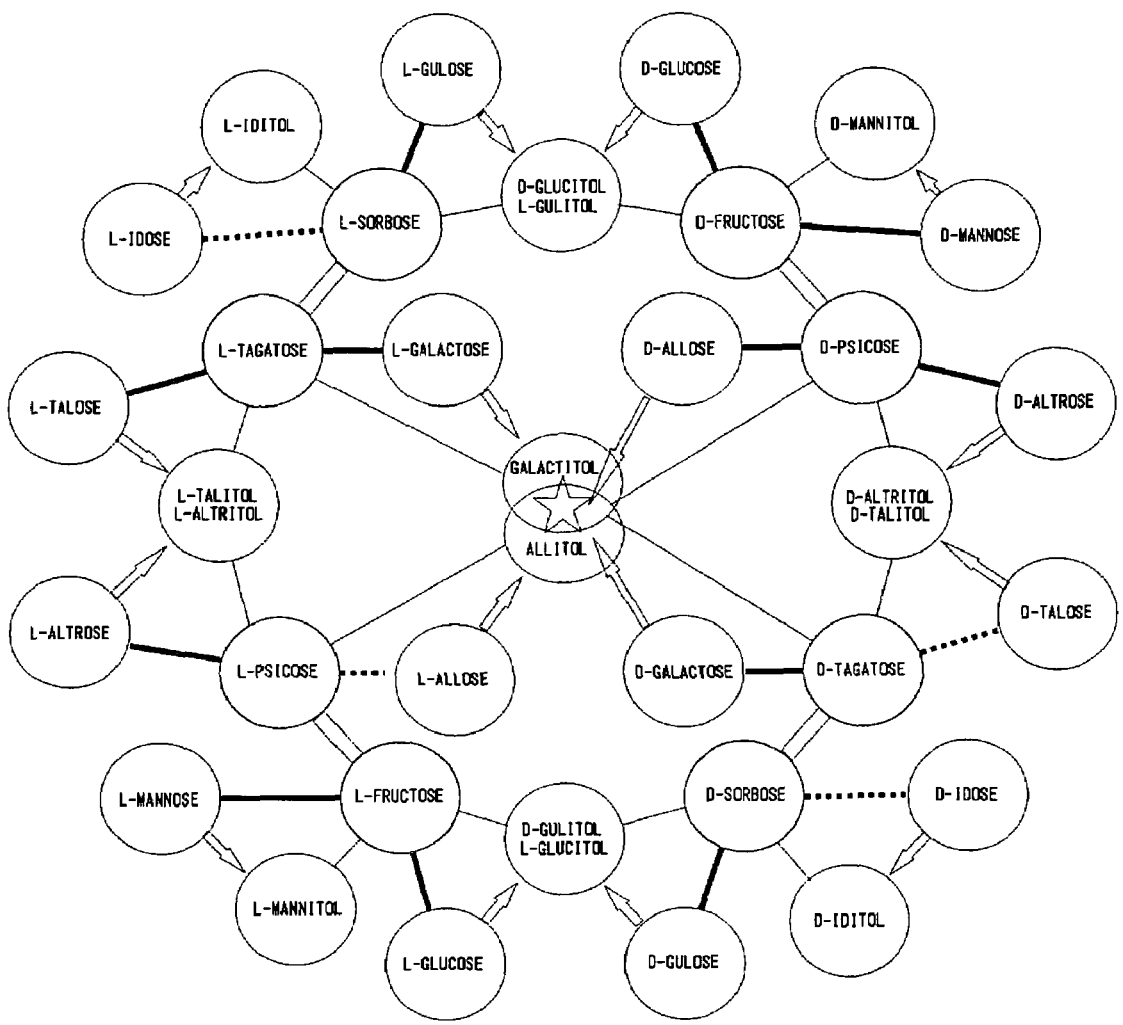

[Fig.8]
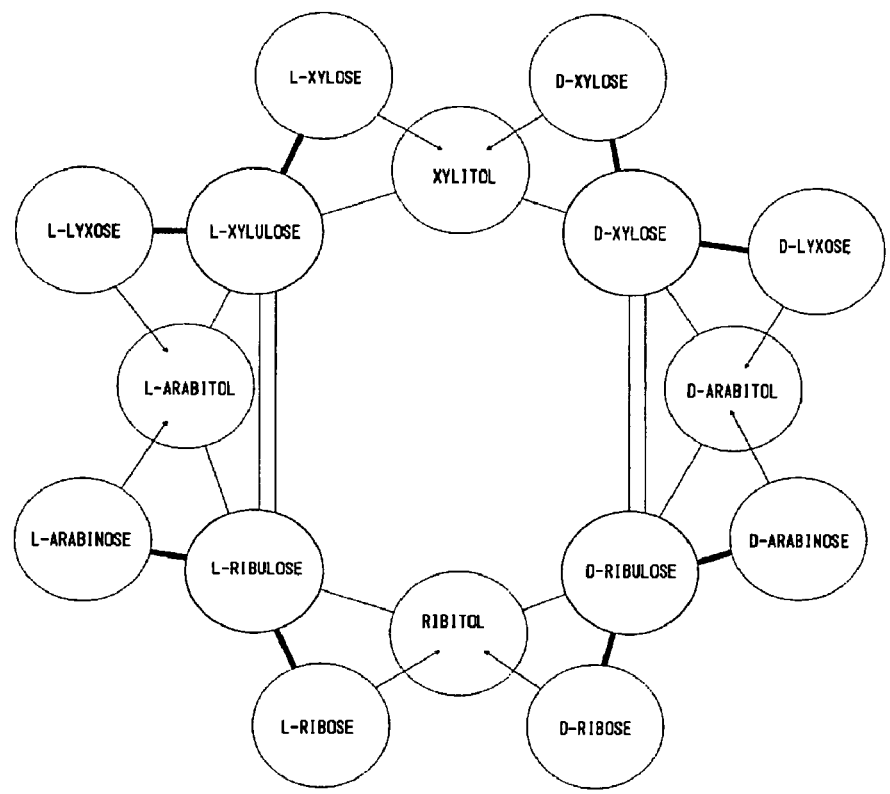
[Fig.9]
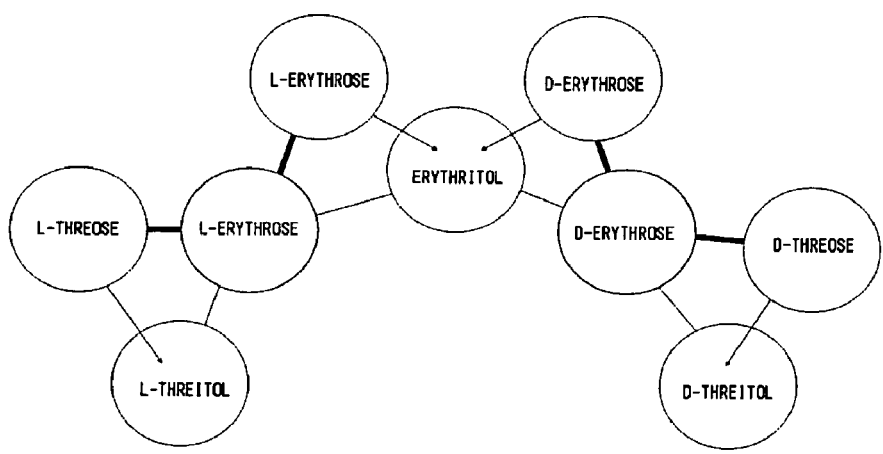

SEQUENCE LISTING

```
<160> NUMBER OF SEQ ID NOS: 7

<210> SEQ ID NO 1
<211> LENGTH: 1257
<212> TYPE: DNA
<213> ORGANISM: Bacillus pallidus

<400> SEQUENCE: 1
atggttataa aagaatctttt tgagatagca aggcaagtct atgaaaaatg gggaataaat      60
attgaagaag tattagaaaa cttgcagcaa gcgtcaatct ctatccattg ctggcaaggt     120
gatgacgtaa aaggatttga agcagatgca agcgagcttt caggggggat tgatgtaaca     180
ggaaattatc cgggaaaggc aagaaatgct gaagaattaa ggcaggattt agagaaagcg     240
```

-continued

```
ctgtcattaa ttccaggaaa acatcgtgtc aacctacacg ccatttatgc agaaacaaat      300
ggtgaaaaag tggaaagaga tcagttagaa ccgaaacatt ttgaaaactg ggttaattgg      360
gcgaaaaaaa ttggtatagg ctggatttt aatcctacct tattttcgca tgaaaaagca       420
gcagatggac tgacgttgtc tcatcctgat ccgggaatta gagaattttg gatcaaccac      480
tgtattagga gccgaaaaat cggtgagtac tttggcaagg agcttggaac accatgctta     540
acaaatatat ggattccgga cggctataag gacattccaa gcgaccgatt gactccaagg     600
aagcgattaa aagaatcatt ggataaaatt tttagtgtag agatcaatga gaaatataat      660
ttggatgcag tcgaaagcaa attgtttgga ataggatctg agtcttttgt tgtcggctcg     720
catgaatttt atctagggta cgccttacaa aataataaaa tatatttatt agatacaggt     780
cattttcatc ctactgaaac agtctcaaat aaaatttcat cgattttgct ttatagcgac     840
aggcttgctt tacacgtatc gagaccggtt cggtgggaca cgaccatgt cgtgattttg      900 gatgatgaat tgcgtgaaat agcacttgaa atcgtgcgca atgatgcgct gcataaggtt     960
ttaatcggac ttgatttctt tgatgccagc atcaatcgtc ttgctgcatg ggtcattgga     1020
acgcgtaata tgattaaagc tttattatat gcaatgctta tgccgcatga atatttaaag     1080
caattgcaag aaaagggaaa ctttacggaa agattggcgg ttatgaggagga atttaaaact   1140 tatcctttcg gtgcaatttg ggattattat tgtgagaaaa tgaatgttcc tgtaagagaa     1200
gaatggttaa agaaattca aaaatatgag gaggaagtat taactaagag acagtag         1257
```

<210> SEQ ID NO 2
<211> LENGTH: 418
<212> TYPE: PRT
<213> ORGANISM: Bacillus pallidus

<400> SEQUENCE: 2

```
Met Val Ile Lys Glu Ser Phe Glu Ile Ala Arg Gln Val Tyr Glu Lys
1               5                   10                  15

Trp Gly Ile Asn Ile Glu Glu Val Leu Glu Asn Leu Gln Gln Ala Ser
            20                  25                  30

Ile Ser Ile His Cys Trp Gln Gly Asp Asp Val Lys Gly Phe Glu Ala
        35                  40                  45

Asp Ala Ser Glu Leu Ser Gly Gly Ile Asp Val Thr Gly Asn Tyr Pro
    50                  55                  60

Gly Lys Ala Arg Asn Ala Glu Glu Leu Arg Gln Asp Leu Glu Lys Ala
65                  70                  75                  80

Leu Ser Leu Ile Pro Gly Lys His Arg Val Asn Leu His Ala Ile Tyr
                85                  90                  95

Ala Glu Thr Asn Gly Glu Lys Val Glu Arg Asp Gln Leu Glu Pro Lys
            100                 105                 110

His Phe Glu Asn Trp Val Asn Trp Ala Lys Lys Ile Gly Ile Gly Leu
        115                 120                 125

Asp Phe Asn Pro Thr Leu Phe Ser His Glu Lys Ala Ala Asp Gly Leu
    130                 135                 140

Thr Leu Ser His Pro Asp Pro Gly Ile Arg Glu Phe Trp Ile Asn His
145                 150                 155                 160

Cys Ile Arg Ser Arg Lys Ile Gly Glu Tyr Phe Gly Lys Glu Leu Gly
                165                 170                 175

Thr Pro Cys Leu Thr Asn Ile Trp Ile Pro Asp Gly Tyr Lys Asp Ile
            180                 185                 190
```

```
Pro Ser Asp Arg Leu Thr Pro Arg Lys Arg Leu Lys Glu Ser Leu Asp
        195                 200                 205

Lys Ile Phe Ser Val Glu Ile Asn Glu Lys Tyr Asn Leu Asp Ala Val
    210                 215                 220

Glu Ser Lys Leu Phe Gly Ile Gly Ser Glu Ser Phe Val Val Gly Ser
225                 230                 235                 240

His Glu Phe Tyr Leu Gly Tyr Ala Leu Gln Asn Asn Lys Ile Tyr Leu
                245                 250                 255

Leu Asp Thr Gly His Phe His Pro Thr Glu Thr Val Ser Asn Lys Ile
            260                 265                 270

Ser Ser Ile Leu Leu Tyr Ser Asp Arg Leu Ala Leu His Val Ser Arg
        275                 280                 285

Pro Val Arg Trp Asp Ser Asp His Val Val Ile Leu Asp Asp Glu Leu
    290                 295                 300

Arg Glu Ile Ala Leu Glu Ile Val Arg Asn Asp Ala Leu His Lys Val
305                 310                 315                 320

Leu Ile Gly Leu Asp Phe Phe Asp Ala Ser Ile Asn Arg Leu Ala Ala
                325                 330                 335

Trp Val Ile Gly Thr Arg Asn Met Ile Lys Ala Leu Leu Tyr Ala Met
            340                 345                 350

Leu Met Pro His Glu Tyr Leu Lys Gln Leu Gln Glu Lys Gly Asn Phe
        355                 360                 365

Thr Glu Arg Leu Ala Val Met Glu Glu Phe Lys Thr Tyr Pro Phe Gly
    370                 375                 380

Ala Ile Trp Asp Tyr Tyr Cys Glu Lys Met Asn Val Pro Val Arg Glu
385                 390                 395                 400

Glu Trp Leu Lys Glu Ile Gln Lys Tyr Glu Glu Val Leu Thr Lys
                405                 410                 415

Arg Gln

<210> SEQ ID NO 3
<211> LENGTH: 1293
<212> TYPE: DNA
<213> ORGANISM: Pseudomonas stutzeri

<400> SEQUENCE: 3
atggctgaat tcaggatcgc tcaggatgtc gttgcgcggg aaaacgacag gcgcgcctcg      60
gcgctgaagg aagactacga ggcgctcggc gcgaatctcg cccgccgtgg cgtcgacatc     120
gaggccgtca cggccaaggt cgaaaagttc ttcgtcgccg tccccctcct gggcgtcggc     180
acgggcggca cgcgctttgc gcgcttcccc ggcaccggcg agccgcgcgg catcttcgac     240
aagctggacg actgcgccgt catccagcag ctgacacgcg ccacgcccaa tgtctcgctg     300
catattccgt gggacaaggc cgatccgaag gagctgaagg ccaggggcga cgccctcggc     360
ctcggcttcg acgcgatgaa ctccaatacc ttctccgatg cgcccggcca ggcgcattcc     420
tacaaatacg gctcgctcag ccacacggat gcggcaacgc gcgcccaggc ggtcgagcac     480
aatctggaat gcatcgagat cggcaaggcc atcggctcca aggcgctgac ggtctggatc     540
ggtgacggct ccaacttccc cggccagagt aacttcacca gggctttcga acgttatctc     600
tcggcgatgg cggagatcta caagggcctg ccgatgact ggaagctgtt ctccgagcac     660
aagatgtacg agccggcctt ctattcgacc gtcgtgcagg actggggcac gaattatctc     720
atcgcccaga cgctcggccc caaggcccag tgcctcgtcg atctcggcca tcacgcgccg     780
aacaccaata tcgagatgat cgtcgcccgg ctcatccagt tcggcaagct cggcggcttc     840
```

-continued

```
catttcaacg attccaaata cggcgacgac gacctcgatg ccggcgccat cgagccctat    900
cgcctcttcc tcgtcttcaa cgagctggtg gatgcggagg cgcgcggcgt caagggcttc    960 caccggccc acatgatcga ccagtcgcac aacgtcaccg acccgatcga gagcctgatc   1020
aacagcgcga acgaaatccg tcgcgcctat gcgcaggccc tccttgtcga ccgcgcggcg   1080
ctttccggct accaggagga caacgacgcc ctgatggcga cggaaacgtt gaagcgcgcc   1140
taccgtaccg atgtggagcc gatcctcgcc gaggcccgcc gccgcacggg cggcgccgtc   1200
gaccccgtcg cgacctatcg ggccagcggc taccgcgcca gggtcgccgc cgagcgcccc   1260
gcctccgtcg cgggtggcgg cggcatcatc tga                                1293
```

<210> SEQ ID NO 4
<211> LENGTH: 430
<212> TYPE: PRT
<213> ORGANISM: Pseudomonas stutzeri

<400> SEQUENCE: 4

```
Met Ala Glu Phe Arg Ile Ala Gln Asp Val Val Ala Arg Glu Asn Asp
1               5                  10                  15

Arg Arg Ala Ser Ala Leu Lys Glu Asp Tyr Glu Ala Leu Gly Ala Asn
            20                  25                  30

Leu Ala Arg Arg Gly Val Asp Ile Glu Ala Val Thr Ala Lys Val Glu
        35                  40                  45

Lys Phe Phe Val Ala Val Pro Ser Trp Gly Val Gly Thr Gly Gly Thr
    50                  55                  60

Arg Phe Ala Arg Phe Pro Gly Thr Gly Glu Pro Arg Gly Ile Phe Asp
65                  70                  75                  80

Lys Leu Asp Asp Cys Ala Val Ile Gln Gln Leu Thr Arg Ala Thr Pro
                85                  90                  95

Asn Val Ser Leu His Ile Pro Trp Asp Lys Ala Asp Pro Lys Glu Leu
            100                 105                 110

Lys Ala Arg Gly Asp Ala Leu Gly Leu Gly Phe Asp Ala Met Asn Ser
        115                 120                 125

Asn Thr Phe Ser Asp Ala Pro Gly Gln Ala His Ser Tyr Lys Tyr Gly
    130                 135                 140

Ser Leu Ser His Thr Asp Ala Ala Thr Arg Ala Gln Ala Val Glu His
145                 150                 155                 160

Asn Leu Glu Cys Ile Glu Ile Gly Lys Ala Ile Gly Ser Lys Ala Leu
                165                 170                 175

Thr Val Trp Ile Gly Asp Gly Ser Asn Phe Pro Gly Gln Ser Asn Phe
            180                 185                 190

Thr Arg Ala Phe Glu Arg Tyr Leu Ser Ala Met Ala Glu Ile Tyr Lys
        195                 200                 205

Gly Leu Pro Asp Asp Trp Lys Leu Phe Ser Glu His Lys Met Tyr Glu
    210                 215                 220

Pro Ala Phe Tyr Ser Thr Val Val Gln Asp Trp Gly Thr Asn Tyr Leu
225                 230                 235                 240

Ile Ala Gln Thr Leu Gly Pro Lys Ala Gln Cys Leu Val Asp Leu Gly
                245                 250                 255

His His Ala Pro Asn Thr Asn Ile Glu Met Ile Val Ala Arg Leu Ile
            260                 265                 270

Gln Phe Gly Lys Leu Gly Gly Phe His Phe Asn Asp Ser Lys Tyr Gly
        275                 280                 285
```

-continued

```
Asp Asp Asp Leu Asp Ala Gly Ala Ile Glu Pro Tyr Arg Leu Phe Leu
        290                 295                 300

Val Phe Asn Glu Leu Val Asp Ala Glu Ala Arg Gly Val Lys Gly Phe
305                 310                 315                 320

His Pro Ala His Met Ile Asp Gln Ser His Asn Val Thr Asp Pro Ile
                325                 330                 335

Glu Ser Leu Ile Asn Ser Ala Asn Glu Ile Arg Arg Ala Tyr Ala Gln
            340                 345                 350

Ala Leu Leu Val Asp Arg Ala Ala Leu Ser Gly Tyr Gln Glu Asp Asn
        355                 360                 365

Asp Ala Leu Met Ala Thr Glu Thr Leu Lys Arg Ala Tyr Arg Thr Asp
370                 375                 380

Val Glu Pro Ile Leu Ala Glu Ala Arg Arg Thr Gly Gly Ala Val
385                 390                 395                 400

Asp Pro Val Ala Thr Tyr Arg Ala Ser Gly Tyr Arg Ala Arg Val Ala
                405                 410                 415

Ala Glu Arg Pro Ala Ser Val Ala Gly Gly Gly Ile Ile
                420                 425                 430
```

<210> SEQ ID NO 5
<211> LENGTH: 424
<212> TYPE: PRT
<213> ORGANISM: Bacillus subtilis

<400> SEQUENCE: 5

```
Met Thr Ile Lys Ala Asn Tyr Asp Ser Ala Lys Gln Ala Tyr Glu Lys
1               5                   10                  15

Trp Gly Ile Asp Val Glu Glu Ala Leu Arg Gln Leu Glu Gln Val Pro
            20                  25                  30

Ile Ser Ile His Cys Trp Gln Gly Asp Asp Ile Glu Gly Phe Glu Val
        35                  40                  45

Asn Lys Gly Glu Leu Ser Gly Ile Asp Val Thr Gly Asn Tyr Pro
    50                  55                  60

Gly Lys Ala Gln Thr Pro Glu Glu Leu Arg Arg Asp Leu Glu Lys Ala
65                  70                  75                  80

Leu Ser Leu Ile Pro Gly Lys His Arg Val Asn Leu His Ala Ile Tyr
                85                  90                  95

Ala Glu Thr Asn Arg Glu Ala Val Glu Arg Asp Glu Leu Lys Pro Gln
            100                 105                 110

His Phe Glu Asn Trp Val Lys Trp Ala Lys Asn Leu Gly Leu Gly Leu
        115                 120                 125

Asp Phe Asn Pro Thr Leu Phe Ser His Glu Lys Ala Ala Asp Gly Leu
    130                 135                 140

Thr Leu Ser His Pro Asp Pro Asp Ile Arg Glu Phe Trp Ile Arg His
145                 150                 155                 160

Cys Ile Ala Cys Arg Arg Ile Gly Glu Tyr Phe Gly Lys Glu Leu Gly
                165                 170                 175

Thr Pro Cys Leu Thr Asn Ile Trp Ile Pro Asp Gly Tyr Lys Asp Ile
            180                 185                 190

Pro Ser Asp Arg Leu Thr Pro Arg Lys Arg Leu Lys Glu Ser Leu Asp
        195                 200                 205

Arg Ile Phe Ser Glu Glu Ile Ser Glu Gln His Asn Leu Asp Ser Ile
    210                 215                 220

Glu Ser Lys Leu Phe Gly Leu Gly Ser Glu Ser Tyr Val Val Gly Ser
225                 230                 235                 240
```

```
His Glu Phe Tyr Leu Ala Tyr Ala Leu Thr Asn His Lys Leu Cys Leu
                245                 250                 255

Leu Asp Thr Gly His Phe His Pro Thr Glu Thr Val Ser Asn Lys Ile
            260                 265                 270

Ser Ser Met Leu Leu Tyr Thr Asp Lys Leu Ala Leu His Val Ser Arg
        275                 280                 285

Pro Val Arg Trp Asp Ser Asp His Val Val Leu Asp Asp Glu Leu
    290                 295                 300

Arg Glu Ile Ala Leu Glu Ile Val Arg Asn His Ala Leu Glu Lys Val
305                 310                 315                 320

Ala Ile Gly Leu Asp Phe Phe Asp Ala Ser Ile Asn Arg Val Ala Ala
                325                 330                 335

Trp Thr Ile Gly Thr Arg Asn Met Ile Lys Ala Leu Leu Tyr Ala Leu
            340                 345                 350

Leu Leu Pro Asn Gly Tyr Leu Lys Gln Leu Gln Glu Glu Gly Arg Tyr
        355                 360                 365

Thr Glu Arg Leu Ala Leu Met Glu Glu Phe Lys Thr Tyr Pro Phe Gly
    370                 375                 380

Ala Ile Trp Asp Ser Tyr Cys Glu Gln Met Gly Val Pro Val Lys Glu
385                 390                 395                 400

Ala Trp Leu Tyr Asp Ile Lys Glu Tyr Glu Gln Val Leu Leu Lys
                405                 410                 415

Arg Lys Ala Ser Ser Pro Ile Val
            420

<210> SEQ ID NO 6
<211> LENGTH: 386
<212> TYPE: PRT
<213> ORGANISM: Streptomyces coelicolor

<400> SEQUENCE: 6

Met Thr Glu Leu Ala Ala Val Lys Ala Leu Lys Thr Gln Ala Val
1               5                   10                  15

Glu Thr Pro Ser Trp Ala Tyr Gly Asn Ser Gly Thr Arg Phe Lys Val
            20                  25                  30

Phe Ala Gln Pro Gly Val Pro Arg Asp Pro Phe Glu Lys Leu Asp Asp
        35                  40                  45

Ala Ala Lys Val His Glu Phe Thr Gly Ala Pro Thr Val Ala Leu
    50                  55                  60

His Ile Pro Trp Asp Arg Val Glu Asp Tyr Ala Ala Leu Ala Ala His
65                  70                  75                  80

Ala Glu Lys Arg Gly Val Arg Ile Gly Ala Ile Asn Ser Asn Thr Phe
                85                  90                  95

Gln Asp Asp Asp Tyr Arg Leu Gly Ser Ile Cys His Pro Asp Ala Ala
            100                 105                 110

Val Arg Arg Lys Ala Val Asp His Leu Leu Glu Cys Val Asp Ile Met
        115                 120                 125

Asp Ala Thr Gly Ser Arg Asp Leu Lys Leu Trp Phe Ala Asp Gly Thr
    130                 135                 140

Asn Tyr Pro Gly Gln Asp Asp Ile Arg Ser Arg Gln Asp Arg Leu Ala
145                 150                 155                 160

Glu Gly Leu Ala Glu Val Tyr Glu Arg Leu Gly Glu Gly Gln Arg Met
                165                 170                 175

Leu Leu Glu Tyr Lys Leu Phe Glu Pro Ala Phe Tyr Thr Thr Asp Val
```

-continued

```
                180                 185                 190
Pro Asp Trp Gly Thr Ala Tyr Ala His Cys Leu Lys Leu Gly Glu Lys
            195                 200                 205
Ala Gln Val Val Val Asp Thr Gly His His Ala Pro Gly Thr Asn Ile
        210                 215                 220
Glu Phe Ile Val Ala Thr Leu Leu Arg Glu Gly Lys Leu Gly Gly Phe
225                 230                 235                 240
Asp Phe Asn Ser Arg Phe Tyr Ala Asp Asp Leu Met Val Gly Ala
                245                 250                 255
Ala Asp Pro Phe Gln Leu Phe Arg Ile Met Tyr Glu Val Val Arg Gly
            260                 265                 270
Gly Gly Phe Thr Ser Asp Val Ala Phe Met Leu Asp Gln Cys His Asn
        275                 280                 285
Ile Glu Ala Lys Ile Pro Ala Ile Ile Arg Ser Val Met Asn Val Gln
290                 295                 300
Glu Ala Thr Ala Lys Ala Leu Leu Val Asp Gly Thr Ala Leu Ala Glu
305                 310                 315                 320
Ala Gln Ala Ala Gly Asp Val Leu Glu Ala Asn Ala Val Leu Met Asp
            325                 330                 335
Ala Tyr Asn Thr Asp Val Arg Pro Leu Leu Arg Glu Val Arg Glu Glu
                340                 345                 350
Ser Gly Leu Asp Pro Glu Pro Met Lys Ala Tyr Arg Ser Cys Gly Trp
            355                 360                 365
Ala Glu Lys Val Val Ala Glu Arg Ile Gly Gln Gln Ala Gly Trp
        370                 375                 380
Gly Ala
385

<210> SEQ ID NO 7
<211> LENGTH: 383
<212> TYPE: PRT
<213> ORGANISM: Thermotoga maritima

<400> SEQUENCE: 7

Met Ile Asn Met Glu Arg Ile Phe Lys Glu Leu Asp Glu Leu Lys Phe
1               5                   10                  15
Glu Leu Pro Ser Trp Ala Phe Ser Asp Ala Gly Thr Arg Phe Ala Val
            20                  25                  30
Phe His Glu Glu Gly Ala Ala Arg Asn Val Phe Glu Arg Ile Glu Asp
        35                  40                  45
Ala Ala Leu Val His Arg Leu Thr Gly Cys Cys Pro Ser Val Ala Leu
    50                  55                  60
His Ile Pro Trp Asp Lys Val Glu Asn Trp Glu Glu Leu Arg Glu Phe
65                  70                  75                  80
Ala Glu Glu Lys Gly Leu Lys Ile Gly Ala Ile Asn Pro Asn Leu Phe
                85                  90                  95
Gln Asp Pro Asp Tyr Lys Tyr Gly Ser Leu Thr Asn Pro Ser Glu Lys
            100                 105                 110
Ile Arg Lys Lys Ala Ile Ala His Val Met Glu Cys Val Asp Ile Ala
        115                 120                 125
Glu Lys Thr Gly Ser Lys Val Ile Ser Leu Trp Leu Ala Asp Gly Thr
    130                 135                 140
Asp Tyr Pro Gly Gln Asp Asp Phe Arg Ser Arg Lys Lys Arg Leu Glu
145                 150                 155                 160
```

-continued

```
Glu Ser Leu Arg Tyr Ile Tyr Glu Asn Met Pro Ala Asp Met Tyr Leu
            165                 170                 175

Leu Ile Glu Tyr Lys Phe Phe Glu Pro Ala Phe Tyr His Thr Asp Ile
            180                 185                 190

Pro Asp Trp Gly Met Ser Tyr Leu Leu Ser Glu Lys Leu Gly Glu Arg
            195                 200                 205

Ala Leu Val Leu Val Asp Leu Gly His His Pro Gln Gly Thr Asn Ile
            210                 215                 220

Glu Tyr Ile Val Ala Thr Leu Leu Ser Glu Lys Lys Leu Gly Gly Phe
225                 230                 235                 240

His Leu Asn Asn Arg Lys Tyr Ala Asp Asp Asp Leu Thr Ile Ala Ser
            245                 250                 255

Ile Asn Pro Tyr Glu Val Phe Leu Ile Phe Lys Glu Ile Val Phe Ala
            260                 265                 270

Lys Arg Asp Pro Glu Leu Ser Asp Ser Ala Lys Lys Val Val Leu Met
            275                 280                 285

Phe Asp Gln Ala His Ile Thr Lys Pro Lys Ile Leu Ala Met Ile Gln
            290                 295                 300

Ser Val Leu Ile Ala Gln Glu Leu Phe Thr Lys Ala Leu Leu Ile Asp
305                 310                 315                 320

Glu Asn Arg Leu Arg Glu Ala Gln Lys Asn Tyr Asp Val Val Glu Ala
            325                 330                 335

Glu Glu Ile Leu Leu Asp Ala Phe Arg Thr Asp Val Arg Pro Ile Leu
            340                 345                 350

Arg Glu Tyr Arg Arg Gln Lys Gly Leu Pro Glu Asp Pro Leu Arg Val
            355                 360                 365

Phe Arg Glu Glu Asp Tyr Met Glu Lys Arg Arg Arg Glu Arg Arg
            370                 375                 380
```

SEQUENCE OF THERMOTOLERANT L-RHAMNOSE ISOMERASE GENE AND USE OF THE SAME

TECHNICAL FIELD

The present invention reveals a gene sequence encoding a thermotolerant L-rhamnose isomerase produced by *Bacillus stearothermophilus*.

L-rhamnose isomerase has been isolated from a variety of microorganisms, and also a gene sequence encoding the same has been reported. In the present invention, when a gene sequence encoding a thermotolerant L-rhamnose isomerase produced by a bacterium (*Bacillus pallidus*) isolated from the soil was determined, it was revealed that the gene sequence does not show homology to any of the gene sequences which have been reported so far and is a novel gene on a gene basis as well as a protein basis.

By utilizing this sequence, a rare sugar can be produced using genetic engineering and it can be applied to the use using various genetic engineering techniques.

Further, the present invention relates to the thermotolerant L-rhamnose isomerase and the application thereof to the production method of a rare sugar such as D-allose.

BACKGROUND ART

L-rhamnose isomerase produced by *Pseudomonas stutzeri* LL172 is a known enzyme having the following physicochemical properties revealed in Non-patent document 1.

(i) Action

It is an enzyme catalyzing an isomerization reaction from L-rhamnose to L-rhamnulose and isomerization from L-rhamnulose to L-rhamnose. It is known that it also acts on isomerization between D-allose and D-psicose (Non-Patent Document 1), and it is an enzyme that can produce D-allose from D-psicose. Isomerases are named based on a substrate against which it exhibits the highest activity and a monosaccharide with which the enzymes are induced, therefore, an enzyme named the same L-rhamnose isomerase were isolated from *E. coli* and *Bacillus subtilis*, and a gene sequence encoding the same has been reported.

(ii) Substrate Specificity

L-rhamnose and L-rhamnulose are used as a substrate. Other than these, L-lyxose and L-xylulose, L-mannose and L-fructose, D-ribose and D-ribulose, D-allose and D-psicose are used as a substrate.

(iii) Working pH and Optimal pH

The working pH thereof ranges from 7.0 to 10.0 and the optimal pH thereof is 9.0.

(iv) pH Stability

It is stable within a pH range of from 6.0 to 11.0 in the case where it is kept at 4° C. for 1 hour at various pH values.

(v) Working Temperature and Optimal Temperature

The working temperature thereof ranges from 40 to 65° C. and a temperature at which the enzyme exhibits the highest activity in the case where a reaction time is 10 minutes is 60° C.

(vi) Temperature Stability

It is stable at 40° C. for 10 minutes and 90% or more of the activity thereof remains even at 50° C. for 10 minutes.

(vii) Effect of Chelating Agent

The activity thereof is hardly inhibited even if it is allowed to coexist with EDTA or EGTA, which is a chelating agent, during the measurement of the activity.

(viii) Effect of Metal Ion

About 30% of the activity thereof is inhibited by 1 mM cobalt ion.

(ix) Molecular Weight by the SDS-PAGE Method

It is about 43,000.

The present inventors revealed a gene sequence (SEQ ID NO: 3) encoding L-rhamnose isomerase produced by *Pseudomonas stutzeri* and separately applied for a patent (Patent document 1). As of the date, L-rhamnose isomerase had been isolated from a variety of microorganisms and also the gene sequence encoding the same had been reported, however, there was no report that L-rhamnose isomerase derived from these reacted with D-psicose thereby to produce D-allose.

When the present inventors determined a gene sequence encoding L-rhamnose isomerase produced by a bacterium (*Pseudomonas stutzeri* LL172) isolated from the soil, it was revealed that the gene sequence does not show homology to any of the gene sequences which have been reported so far and is a novel gene on a gene basis as well as a protein basis (see FIGS. 4 to 6). By utilizing this sequence, an enzyme is produced in a large amount by using genetic engineering and the production of a rare sugar can be carried out using the produced enzyme, or this sequence can be applied to the use using various genetic engineering techniques other than this. Further, the present inventors advanced the studies and revealed that L-rhamnose isomerase produced by *Pseudomonas stutzeri* has a new catalytic function catalyzing an isomerization reaction of a sugar, which had not been found so far.

The protein described in Patent document 1 is a protein as follows:

(1) a protein comprising an amino acid sequence represented by SEQ ID NO: 4; or (2) a protein comprising an amino acid sequence in which one or several amino acids have been deleted, substituted or added in the amino acid sequence represented by SEQ ID NO: 4 and having an L-rhamnose isomerase activity; and (3) the L-rhamnose isomerase activity is specified by the following physicochemical properties.

(i) Action

It catalyzes an isomerization reaction represented by any of the thick black lines in FIG. 7, FIG. 8 and FIG. 9.

(ii) Working pH and Optimal pH

The working pH thereof ranges from 7.0 to 10.0 and the optimal pH thereof is 9.0.

(iii) pH Stability

It is stable within a pH range of from 6.0 to 11.0 in the case where it is kept at 4° C. for 1 hour at various pH values.

(iv) Working Temperature and Optimal Temperature

The working temperature thereof ranges from 40 to 65° C. and a temperature at which the enzyme exhibits the highest activity in the case where a reaction time is 10 minutes is 60° C.

(v) Temperature Stability

It is stable at 40° C. for 10 minutes and 90% or more of the activity thereof remains even at 50° C. for 10 minutes.

(vi) Effect of Chelating Agent

The activity thereof is hardly inhibited even if it is allowed to coexist with EDTA or EGTA, which is a chelating agent, during the measurement of the activity.

(vii) Effect of Metal Ion

About 30% of the activity thereof is inhibited by 1 mM cobalt ion.

(viii) Molecular Weight by the SDS-PAGE Method

It is about 43,000.

In a conventional production method using an enzymatic reaction method involved in the conversion of D-psicose to D-allose according to the present inventors, in the case where a bioreactor is used, the reaction temperature in the bioreactor is important. That is, when the reaction temperature in the bioreactor is low, contamination with microorganisms during the reaction is caused, and not only is the enzymatic activity decreased, but also the purity or the yield of the product is significantly decreased. Due to this, an industrially important object to be achieved is to carry out a reaction by raising the reaction temperature. Further, in order to maintain the temperature in the bioreactor at room temperature, there is a need to cool the bioreactor in the case of industrial implementation. Energy to be used for cooling the bioreactor is large, which leads to an increase in the cost. From this viewpoint, it becomes an important object for the production of D-allose to raise the reaction temperature.

Patent Document 1: WO 2004/063369

Patent Document 2: JP-A-2002-17392

Non-Patent Document 1: "Journal of Fermentation and Bioengineering", Vol. 85, pp. 539 to 541 (1998)

DISCLOSURE OF THE INVENTION

Problems that the Invention is to Solve

A major object is to realize the reduction of contamination with microorganisms and energy to be used for cooling by raising an operating temperature of a bioreactor even a little. Further, the pH during the reaction is also important. It is general that when a reaction at a high concentration is carried out, a decrease in the pH is caused during the conversion of a sugar in general. It can be said that another object to be achieved is to establish a condition in which the reaction can be continuously carried out without causing the inactivation of the enzyme even if it is exposed to a low pH at this time.

L-rhamnose isomerase derived from *Pseudomonas stutzeri* is an enzyme catalyzing an isomerization reaction between L-rhamnose and L-rhamnulose, and it has been already known that it also catalyzes an isomerization reaction between D-psicose and D-allose. In the present invention, an object is to obtain a novel enzyme which has a higher reaction efficiency between D-psicose and D-allose and is excellent in thermal stability.

To produce a rare sugar in a large amount is the basis of the studies of rare sugars performed by the present inventors. The present invention is directed to making the reaction efficiency between D-psicose and D-allose higher by increasing the reaction temperature in the enzymatic reaction method involved in the conversion of D-psicose to D-allose.

An object of the present invention is to provide a gene sequence of a novel and useful thermotolerant L-rhamnose isomerase and to allow it to be applied to the production of a rare sugar using genetic engineering and the use using various genetic engineering techniques.

Means for Solving the Problems

It is considered that a search for an enzyme that can react at a higher temperature than L-rhamnose isomerase derived from *Pseudomonas stutzeri* which is the only enzyme that has been conventionally known to be able to be used for producing D-allose from D-psicose is one of the methods for achieving the above objects. L-rhamnose isomerase produced by *E. coli* can react at a higher temperature than L-rhamnose isomerase derived from *Pseudomonas stutzeri*, however, this enzyme hardly exhibits an activity of producing D-allose from D-psicose, therefore, it cannot be used.

We made a search for microorganisms growing at a high temperature, and found that L-rhamnose isomerase produced by one strain (FERM BP-10407) among them is a thermotolerant enzyme that has an ability to catalyze a reaction from D-psicose to D-allose in the same manner as L-rhamnose isomerase derived from *Pseudomonas stutzeri* and reacts at a high temperature, and thus the present invention could be completed. That is, the present invention reveals the gene sequence encoding the thermotolerant L-rhamnose isomerase produced by *Bacillus stearothermophilus*, which was found to be *Bacillus pallidus* later. When the gene sequence encoding the thermotolerant L-rhamnose isomerase produced by a bacterium (*Bacillus pallidus*) isolated from the soil was determined, it was found that the gene sequence does not show homology to any of the gene sequences which have been reported so far and is a novel gene on a gene basis as well as a protein basis.

By utilizing this sequence, a rare sugar can be produced using genetic engineering and it can be applied to the use using various genetic engineering techniques.

The objects can be achieved by providing a DNA encoding the thermotolerant L-rhamnose isomerase derived from *Bacillus pallidus* that catalyzes an isomerization reaction from L-rhamnose to L-rhamnulose and also an isomerization reaction from L-rhamnulose to L-rhamnose, and a method for producing a polypeptide by a recombinant DNA technique using the DNA.

That is, a gist of the present invention is a DNA according to any of the following (1) to (5).

(1) A DNA encoding the following protein (a) or (b):

(a) a protein comprising an amino acid sequence represented by SEQ ID NO: 2;

(b) a protein comprising an amino acid sequence in which one or several amino acids have been deleted, substituted or added in the amino acid sequence represented by SEQ ID NO: 2 and having an L-rhamnose isomerase activity.

(2) A DNA comprising a base sequence represented by SEQ ID NO: 1 or a complementary sequence thereto or a sequence containing a part or the whole of any of these sequences.

(3) A DNA hybridizing to the DNA according to the above (2) under a stringent condition and encoding a protein having an L-rhamnose isomerase activity.

(4) The DNA according to the above (1), (2) or (3), which is L-rhamnose isomerase derived from *Bacillus pallidus*.

(5) The DNA according to the above (4), which is derived from *Bacillus pallidus* strain 14a (FERM BP-10407).

Further, a gist of the present invention is a protein according to any of the following (6) to (11).

(6) A protein comprising an amino acid sequence represented by SEQ ID NO: 2.

(7) A protein comprising an amino acid sequence in which one or several amino acids have been deleted, substituted or added in the amino acid sequence represented by SEQ ID NO: 2 and having an L-rhamnose isomerase activity.

(8) The protein according to the above (6) or (7), which has an L-rhamnose isomerase activity specified by the following substrate specificity and physicochemical properties.

(i) Substrate Specificity

It has a substrate specificity in that the relative percentages of the enzymatic activities thereof against L-lyxose, L-mannose and D-allose are 23.9%, 11% and 5.5%, respectively, when the enzymatic activity thereof against L-rhamnose is assumed to be 100%.

(ii) Action

It catalyzes an isomerization reaction from D-psicose to D-allose.

(iii) Working pH and Optimal pH

The working pH thereof ranges from 6 to 10 and a pH at which the enzymatic activity thereof is the highest (optimal pH) ranges from 6 to 9.

(iv) pH Stability

It is stable within a pH range of from 6 to 9 in terms of the effect of pH on the enzymatic activity thereof.

(v) Optimal Temperature and Working Temperature

A temperature at which the enzymatic activity thereof is the highest (optimal temperature) is 80° C. and the working temperature thereof ranges from 30 to 80° C.

(vi) Temperature Stability

It is stable up to 50° C. in the case of a heat treatment condition of 1 hour in terms of the effect of temperature on the enzymatic activity thereof.

(vii) Effect of Metal Ion

About 30% of the activity thereof is inhibited by 1 mM cobalt ion.

(viii) Molecular Weight

The molecular weight of a monomer is about 45,000, and it is a tetramer composed of 4 subunits and having a molecular weight of about 180,000.

(9) The protein according to the above (6), (7) or (8), which is derived from *Bacillus pallidus* strain 14a (FERM BP-10407).

(10) The protein according to the above (9), which has a substrate specificity as follows compared with the substrate specificity of L-rhamnose isomerase produced by *Pseudomonas stutzeri* LL172 (FERM BP-08593).

It has substantially the same substrate specificity in that the relative percentages of the enzymatic activities thereof against L-lyxose, L-mannose and D-allose are 23.9% (43.9% in the case of the L-rhamnose isomerase produced by LL172), 11% (33.4% in the case of the L-rhamnose isomerase produced by LL172) and 5.5% (7.2% in the case of the L-rhamnose isomerase produced by LL172), respectively, when the enzymatic activity thereof against L-rhamnose is assumed to be 100%.

(11) The protein according to the above (9) or (10), which has enzymological properties as described in the following (a) and (b) compared with the enzymological properties of L-rhamnose isomerase produced by *Pseudomonas stutzeri* LL172 (FERM BP-08593).

(a) A temperature at which the enzymatic activity thereof is the highest (optimal temperature) is 80° C. in a reaction time of 10 minutes, which is higher by 20° C. compared with 60° C. in the case of the L-rhamnose isomerase produced by LL172, and it is stable up to 50° C. in the case of a heat treatment condition of 1 hour in terms of the effect of temperature on the enzymatic activity thereof, which is also higher by 10° C. compared with 40° C. in the case of the L-rhamnose isomerase produced by LL172.

(b) A pH at which the enzymatic activity thereof is the highest (optimal pH) ranges from 6 to 9, and it has a characteristic that the activity thereof is high even in an acidic region compared with the L-rhamnose isomerase produced by LL172, which has an optimal pH of from 8 to 9, and it is stable within a pH range of from 6 to 9 in terms of the effect of pH on the enzymatic activity thereof, and has a characteristic that it is stable even in an acidic region compared with the L-rhamnose isomerase produced by LL172, which is stable within a pH range of from 7 to 9.

Further, a gist of the present invention is a fusion protein according to the following (12).

(12) A fusion protein in which the protein according to any one of the above (6) to (9) has been bound to a protein translation initiation codon.

Further, a gist of the present invention is a recombinant vector according to the following (13).

(13) A recombinant vector containing the DNA according to any one of the above (1) to (5).

Further, a gist of the present invention is a host cell according to the following (14).

(14) A host cell containing an expression system capable of expressing the protein according to any one of the above (6) to (11).

Further, a gist of the present invention is a method for producing a recombinant protein according to the following (15).

(15) A method for producing a recombinant protein characterized by culturing the host cell containing an expression system according to the above (14) in a medium and collecting a recombinant protein having an L-rhamnose isomerase activity from the thus obtained culture.

Further, a gist of the present invention is a method for producing a rare sugar according to any of the following (16) to (18).

(16) A method for producing a rare sugar, wherein a variety of rare sugars are produced by utilizing an ability of isomerization with a wide range of specificity of the protein having an L-rhamnose isomerase activity according to any one of the above (6) to (11).

(17) The method for producing a rare sugar according to the above (16), wherein D-psicose is converted to D-allose by allowing the protein having an L-rhamnose isomerase activity to act on a solution containing D-psicose as a catalyst, whereby D-allose is produced.

(18) The method for producing a rare sugar according to the above (17), wherein the protein is allowed to act on the solution at 50 to 80° C.

Advantage of the Invention

By a genetic engineering technique, L-rhamnose isomerase can be produced in a large amount, and a mass production method of a variety of rare sugars including D-allose using the enzyme of the present invention can be established.

The present invention can provide a novel enzyme which has a higher reaction efficiency between D-psicose and D-allose and is excellent in thermal stability.

According to the present invention, it is possible to make the reaction efficiency higher between D-psicose and D-allose by raising the reaction temperature in the enzymatic reaction method involved in the conversion of D-psicose or the like to D-allose and to construct a bioreactor with which an industrial production cost is made lower than that of the conventional production of D-allose using L-rhamnose isomerase derived from *Pseudomonas stutzeri* by utilizing the enzyme which has an activity and is stable within a relatively wide pH range.

As shown in the substrate specificity of the protein having an L-rhamnose isomerase activity derived from *Pseudomonas stutzeri*, at least the activities of (L-xylulose→) L-lyxose, (L-fructose), L-mannose, (D-xylulose→) D-lyxose have been confirmed. This indicates that the respective rare sugars can be produced. However, the production of any of the rare sugars using a thermotolerant enzyme has not been reported yet.

Therefore, the present invention can provide a method for producing a variety of rare sugars, characterized by utilizing an ability of isomerization with a wide range of specificity of the protein having an L-rhamnose isomerase activity derived from *Bacillus pallidus*.

Best Mode For Carrying Out The Invention

*Bacillus pallidus* strain 14a is a bacterium isolated from the soil in Kagawa prefecture. The scientific properties of the strain are as follows. It is a gram-positive spore-bearing bacterium which is thermophilic in that it does not have an ability to grow at body temperature or a low temperature and has a growth temperature of 50° C. or higher as an optimal temperature, and is aerobic in that oxygen is required for its growth. It belongs to the bacillus group. As for the taxonomic position thereof, it was classified as *Bacillus stearothermophilus* in the family Bacillaceae, and later it was found to be classified as *Bacillus pallidus* by a genetic engineering technique.

The bacteriological properties of the strain are as follows. Because these properties coincide with those of *Bacillus pallidus* described generally, it was identified as *Bacillus pallidus*.

Gram staining: positive
Morphology: bacillus
Mobility: +
Catalase production: +
Growth in 7% NaCl: Impossible
Starch-degrading ability: +
Spore-forming ability: +
From glucose,
Acid production: +
Gas production: −
Growth temperature: the highest temperature: 65° C., the lowest temperature: 35° C.
Spore formation
An oval spore is formed after 3 days.
Form of colony (culture conditions medium used: meat extract, culture temperature: 55° C., culture period: 1 day)
Diameter: 5 mm
Color: white
Shape: circular
Protrusion state: flat
Peripheral part of colony: entire fringe
Form of surface: smooth
Transparency: Not transparent
Viscosity: like butter
Polymorphism of colony
Change in the form of colony due to mutation:
Change in the form of colony due to culture conditions or physiological states:

The strain belonging to *Bacillus stearothermophilus*, which was found to belong to *Bacillus pallidus* later (*Bacillus stearothermophilus* strain 14a, later *Bacillus pallidus* strain 14a, which was identified by a genetic engineering technique) was domestically deposited at the International Patent Organism Depositary, National Institute of Advanced Industrial Science and Technology (Central 6, 1-1-1 Higashi, Tsukuba-shi, Ibaraki-ken, Japan) on Aug. 19, 2004 (FERM AP-20172), which was transferred from domestic deposit to international deposit on Aug. 23, 2005 (FERM BP-10407).

The thermotolerant L-rhamnose isomerase as used in the present invention is a thermotolerant L-rhamnose isomerase derived from *Bacillus pallidus* strain 14a (FERM BP-10407) and has an amino acid sequence represented by SEQ ID NO: 2 or an amino acid sequence in which one or more amino acids in the amino acid sequence represented by SEQ ID NO: 2 have been substituted with another amino acid, deleted, or one or more amino acids have been added thereto. The gene (DNA) as used in the present invention has a base sequence encoding the above L-rhamnose isomerase.

That is, as the protein to be a subject of the present invention, a protein (a thermotolerant L-rhamnose isomerase) comprising an amino acid sequence represented by SEQ ID NO: 2 and a protein comprising an amino acid sequence in which one or several amino acids have been deleted, substituted or added in the amino acid sequence represented by SEQ ID NO: 2 and having an L-rhamnose isomerase activity can be exemplified.

As the DNA to be a subject of the present invention, a DNA encoding a protein comprising an amino acid sequence represented by SEQ ID NO: 2 or a protein comprising an amino acid sequence in which one or several amino acids have been deleted, substituted or added in the amino acid sequence represented by SEQ ID NO: 2 and having an L-rhamnose isomerase activity, a DNA comprising a base sequence represented by SEQ ID NO: 1 or a complementary sequence thereto or a part or the whole of any of these sequences and a DNA hybridizing to such a DNA under a stringent condition and encoding a protein having an L-rhamnose isomerase activity can be exemplified as preferred examples.

Such a DNA can be prepared by a known method from a gene library or the like based on the information of its DNA sequence. In addition, by using the base sequence represented by SEQ ID NO: 1 or a complementary sequence thereto or a part or the whole of any of these sequences as a probe, hybridization to a DNA library derived from a variety of cells is carried out under a stringent condition, and a DNA hybridizing to the probe is isolated, whereby a DNA encoding a protein having an L-rhamnose isomerase activity can also be obtained. As the hybridization condition for obtaining such a DNA, for example, hybridization at 42° C. and a washing treatment at 42° C. with a buffer containing 1×SSC and 0.1% SDS can be exemplified, and hybridization at 65° C. and a washing treatment at 65° C. with a buffer containing 0.1×SSC and 0.1% SDS can be preferably exemplified. Incidentally, as a factor that has an influence on the stringency of hybridization, there are various factors other than the above-mentioned temperature condition, and it is possible to realize a stringency equivalent to the stringency of hybridization illustrated above by appropriately combining various factors.

The fusion protein of the present invention may be any as long as it is a fusion protein in which the above-mentioned protein of the present invention binds to a protein translation codon. The protein translation codon is not particularly limited as long as it is a conventionally known protein translation codon. Such a fusion protein can be prepared by a standard method, and is useful also as a reagent for research purposes in this field.

In addition, the present invention relates to a host cell containing an expression system capable of expressing the above-mentioned protein of the present invention. Introduction of a gene encoding such a protein of the present invention into a host cell can be carried out by a method described in many standard laboratory manuals such as Davis et al. (BASIC METHODS IN MOLECULAR BIOLOGY, 1986) and Sambrook et al. (MOLECULAR CLONING: A LABORATORY MANUAL, 2nd Ed., Cold Spring Harbor Laboratory Press, Cold Spring Harbor, N.Y., 1989). As the host cell, bacterial prokaryotic cells such as *E. coli, Streptomyces, Bacillus subtilis, Streptococcus* and *Staphylococcus*, other cells can be exemplified.

In addition, the expression system may be any expression system as long as it is an expression system capable of expressing the above-mentioned protein of the present invention in a host cell. Examples of the expression system may include expression systems derived from chromosomes, episomes and viruses, for example, vectors derived from bacterial plasmids, yeast plasmids, papovaviruses such as SV40, vaccinia viruses, adenoviruses, chicken pox viruses, pseudorabies viruses and retroviruses, vectors derived from bacteriophages, transposons, and the combination thereof, for example, vectors derived from genetic factors of plasmids and bacteriophages such as cosmids and phagemids. These expression systems may contain a regulatory sequence that not only causes expression but also regulates expression.

The protein of the present invention obtained by culturing a host cell that contains any of the above-mentioned expression systems can be used in the production of D-allose. In addition, for collecting the protein of the present invention from the cell culture and purifying the protein, any of known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography, preferably high performance liquid chromatography can be used.

The production of L-rhamnose isomerase derived from *Bacillus pallidus* strain 14a will be described.

*Bacillus pallidus* strain 14a is inoculated into a yeast extract medium (pH 7.0), and aerobic shaking culture is carried out at 55° C. for 2 days.

Then, by using the alumina grinding method, the cultured cells in the form of a bar are ground, and a crude enzyme is extracted with a Tris-HCl buffer (pH 8.5).

Purification of the enzyme comprises Steps 1 to 4.

Step 1: A protein which is precipitated with 15% polyethylene glycol 6000 is removed and the enzyme of interest is obtained in the supernatant.

Step 2: By using a Q-Sepharose HP 16/20 anion exchange column equilibrated in advance with the same Tris-HCl buffer (pH 8.5) as used for the enzyme solution, separation is carried out with a sodium chloride gradient, whereby a fraction containing the enzyme of interest is obtained.

Step 3: By using a Phenyl-Sepharose HP 16/20 hydrophobic column equilibrated in advance with a Tris-HCl buffer (pH 8.5) containing 2 M ammonium sulfate, separation is carried out with an ammonium sulfate gradient, whereby a fraction containing the enzyme of interest is obtained.

Step 4: After desalting, by using a Mono Q anion exchange column equilibrated in advance with a 20 mM Tris-HCl buffer (pH 7.5), separation is carried out with a sodium chloride gradient, whereby a fraction containing the enzyme of interest is obtained.

By the purification described above, the enzyme is purified to about 6-fold and a purified preparation can be obtained at a yield of about 12%.

L-rhamnose isomerase produced by *Pseudomonas stutzeri* LL172 (IPOD FERM BP-08593) to be compared with a protein having an L-rhamnose isomerase activity derived from *Bacillus pallidus* strain 14a (IPOD FERM AP-10407) will be described.

"*Pseudomonas stutzeri* LL172" strain belonging to the genus *Pseudomonas stutzeri* is a known bacterium described in the above-mentioned documents, and stored in the Ken Izumori Laboratory, Kagawa University Rare Sugar Research Center. This strain was internationally deposited at the International Patent Organism Depositary, National Institute of Advanced Industrial Science and Technology (Central 6, 1-1-1 Higashi, Tsukuba-shi, Ibaraki-ken, Japan) on Jan. 6, 2004 (IPOD FERM BP-08593). Incidentally, this strain is sometimes represented by LL172a, however, LL172 and LL172a are the same strain.

L-rhamnose isomerase is an enzyme catalyzing an isomerization reaction from L-rhamnose to L-rhamnulose and isomerization from L-rhamnulose to L-rhamnose. L-rhamnose isomerase produced by *Pseudomonas stutzeri* LL172 also acts on isomerization between D-allose and D-psicose, therefore, it is an enzyme that can produce D-allose from D-psicose. Incidentally, in order to produce D-allose from D-psicose, an enzyme derived from *Pseudomonas stutzeri* LL172 (IPOD FERM BP-08593) is needed. The gene sequence encoding L-rhamnose isomerase derived from *Pseudomonas stutzeri* LL172 does not show homology to the gene sequences encoding L-rhamnose isomerases which have been reported so far, and it was found to be a novel gene on a gene basis as well as a protein basis.

L-rhamnose isomerase derived from *Pseudomonas stutzeri* LL172 (FERM BP-08593) has the amino acid sequence represented by SEQ ID NO: 4 (see FIG. 4) or an amino acid sequence in which one or more amino acids in the amino acid sequence represented by SEQ ID NO: 4 have been substituted with another amino acid, deleted, or one or more amino acids have been added thereto.

In addition, as the above-mentioned L-rhamnose isomerase activity, an enzymatic activity catalyzing an isomerization reaction from L-rhamnose to L-rhamnulose and isomerization from L-rhamnulose to L-rhamnose can be preferably exemplified. Further, an enzymatic activity catalyzing isomerization between D-allose and D-psicose can be exemplified. There is no report on the activity that can produce D-allose from D-psicose other than L-rhamnose isomerase derived from *Pseudomonas stutzeri* LL172.

D-allose is a rare sugar which has been found to particularly have a variety of bioactivities in the process of studies of rare sugars (see FIG. 7). Rare sugars can be defined as monosaccharides and sugar alcohols that exist only in a small amount in nature. There are 7 types of monosaccharides that exist in a large amount in nature, i.e., D-glucose, D-fructose, D-galactose, D-mannose, D-ribose, D-xylose and L-arabinose, and all the other monosaccharides are rare sugars (see FIGS. 7 to 9). In addition, a sugar alcohol can be produced by reducing a monosaccharide, however, D-sorbitol exists in a relatively large amount in nature, and the others exist in a small amount, therefore, these can be a rare sugar. D-allose (D-allohexose) to be a subject of collection by separation in the present invention is a D-form of allose classified as aldose (aldohexose), and it is a hexose ($C_6H_{12}O_6$) having a melting point of 178° C.

Examples of a production method of D-allose include a production method by a method of reducing D-allonic acid lactone with sodium amalgam and a production method of synthesizing D-allose from D-psicose using L-rhamnose isomerase as described in Shakkawat Hossain Bhuiyan et al., "Journal of Fermentation and Bioengineering", Vol. 85, pp. 539 to 541 (1993). Further, in recent years, a method is described in JP-A-2002-17392, in which a production method of producing D-allose from D-psicose by allowing D-xylose isomerase to act on a solution containing D-psicose is invented. According to the production method described in JP-A-2002-17392, in the case where D-allose is produced, it is obtained as an enzyme reaction solution containing newly produced D-allose together with unreacted D-psicose.

In the present invention, by using a solution containing a substrate as a raw material, reaction is carried out at 60 to 80°C. by an enzymatic reaction using a protein having an L-rhamnose isomerase activity derived from *Bacillus palli-* dus strain 14a (IPOD FERM BP-10407), and D-allose can be efficiently obtained as a solution containing D-allose. Further, from this solution containing D-allose, D-allose can be collected by separation. Further, the above-mentioned reaction can be continuously carried out to produce D-allose.

As for the enzyme to be used in the conversion of a substrate that can be converted into D-allose into D-allose by the enzymatic reaction, "L-rhamnose isomerase" which is a protein having an L-rhamnose isomerase activity derived from the above-mentioned *Bacillus pallidus* strain 14a (IPOD FERM BP-10407) is used as an enzyme that can produce D-allose from D-psicose in the present invention.

The principle of the collection by separation will be briefly described. D-psicose and D-allose are both readily soluble in water. D-psicose has a solubility of about 10% in methanol and ethanol, however, D-allose is insoluble in either alcohol. The temperature has an influence on the solubility. The solubility of D-psicose in both alcohols is increased at a high temperature. Further, when the alcohol concentration is high, D-allose is likely to be crystallized. It is a separation technique utilizing the above physical properties. It is a production method of high-purity D-allose in which by allowing an alcohol (methanol and/or ethanol) to act on, D-allose which is insoluble in the alcohol (methanol and/or ethanol) is crystallized and the crystal of D-allose is separated.

Also in the case where a glycine buffer (pH 9.0) and 1 mM $MnCl_2$ contained in the enzymatic reaction solution are not removed upon allowing the alcohol (methanol and/or ethanol) to act on, the same results can be obtained.

A continuous method will be briefly described.

An immobilized enzyme which is stable even in a 50% ethanol solution is used. As the immobilized enzyme, one obtained by, for example, immobilizing L-rhamnose isomerase by the covalent bonding method is used. In the case where the enzyme extracted from the bacterial cell is used, after the enzyme is precipitated, in the case where the bacterial cell itself is used, as it is, crosslinking is carried out with glutaraldehyde. In this process, crosslinking is affected through covalent bonding, and by adding lysine thereto, the strength thereof can be further increased. By this immobilization method, an immobilized enzyme with stability for several months can be obtained, compared with a conventional method which achieved the stability for at most 1 week. The immobilized enzyme and/or immobilized microorganism obtained by immobilizing L-rhamnose isomerase by the covalent bonding method are/is furnished to a bioreactor to be used, whereby a bioreactor in which the immobilized enzyme that is stable even in a 50% ethanol solution is used can be constructed. By furnishing a D-psicose solution containing 50% ethanol using the bioreactor in which the immobilized enzyme that is stable even in a 50% ethanol solution is used, the crystal of D-allose is continuously produced by controlling the temperature at 42° C. during the reaction and 4° C. during the crystallization. The filtrate after the crystallization is added to the bioreactor again without removing ethanol or performing concentration.

It is an innovative method with which only D-allose can be separated by adding ethanol to a mixed solution of D-psicose and D-allose. Moreover, it is not necessary to remove a buffer to be used for the enzymatic reaction, therefore, there is a great advantage that labor in the separation step can be saved to a large extent and the separation step can be made more efficient. In the case where D-allose is produced in an enzymatic reaction by using 50% D-psicose as a raw material, the product is obtained as a mixed solution containing 35% D-psicose and 15% D-allose. It is possible to obtain high-purity D-allose by rapidly separating D-psicose and D-allose from the enzymatic reaction product. It became possible to remove the biggest obstacle in the production of D-allose.

The conventional production methods according to the present inventors using the enzymatic reaction method involved in the conversion of D-psicose or the like to D-allose are not yet completely satisfactory in terms of the collection of D-allose by separation, and still require uneconomical operation from the viewpoint of industrial production. The production of D-allose had been carried out from D-psicose with the use of L-rhamnose isomerase so far by a method in which separation is carried out using a simulated moving bed chromatography after a step of removing a buffer from a reaction solution in which D-psicose and D-allose are mixed. D-psicose exhibits a broad behavior with a broad peak in a separation column, therefore, when the separation is carried out, a large amount of water is required. Accordingly, concentration is carried out to evaporate a large amount of water, which is a step requiring an enormous cost and consuming the maximum energy as a whole. Further, the step of separating a buffer or the like from the enzymatic reaction solution is also complicated, and a deionization reaction is a step requiring energy. In order to improve this step, the present inventors examined how the most energy-consuming step is carried out efficiently, which was discovered during the research and development for achieving the most important object for the production of a rare sugar. The characteristic of this invention is that a step of concentration is hardly needed and also a step of removing a buffer in the enzymatic reaction is not needed, and there is a great advantage that the entire operation is extremely simple.

It is possible to obtain a crystal of D-allose by directly adding the product of the enzymatic reaction using the bioreactor dropwise to an ethanol solution. Further, using a system in which the ethanol solution is exchanged at a regular time interval, full automation can be achieved from the step of furnishing D-psicose to the step of obtaining the crystal of D-allose. Further, if a bioreactor in which an immobilized enzyme that is stable even in a 50% ethanol solution is used can be constructed, by furnishing a D-psicose solution containing 50% ethanol, a crystal of D-allose can be continuously obtained by controlling the temperature at 42° C. during the reaction and at 4° C. during the crystallization, and also the filtrate after the crystallization can be added to the bioreactor again without removing the alcohol or performing concentration.

By cooling the reaction solution to an appropriate temperature after completion of the reaction of D-psicose to D-allose, only D-allose is deposited. D-psicose present in the buffer containing ethanol, which is the supernatant, can be used for the reaction again. At this time, by newly adding D-psicose to be a raw material, D-allose can be continuously produced.

The invention of this application will be described in detail with reference to Examples. The invention of this application is by no means limited to these Examples.

EXAMPLE 1

(Preparation of Enzyme)

<Method and Results>

Culture Condition of Microorganism

*Bacillus stearothermophilus* strain 14a (=*Bacillus pallidus* strain 14a) was inoculated into a yeast extract medium (pH 7.0) (0.5% yeast extract, 0.5% peptone, 0.5% NaCl, 3% L-sodium glutamate and 0.5% L-rhamnose), and aerobic shaking culture was carried out at 55° C. for 2 days.

Extraction of Crude Enzyme

Extraction of an enzyme from the microorganism was carried out by the alumina grinding method. That is, alumina and 7.59 g of bacterial cells were mixed in a mortar and ground for 30 minutes with a pestle, and extraction of enzyme was carried out with a 20 mM Tris-HCl buffer (pH 8.5), whereby 50 ml of a crude enzyme was obtained.

Purification of Enzyme

Step 1

A protein precipitated by gradually adding 15% polyethylene glycol 6000 ground into a powder to the crude enzyme solution was removed. The majority of the enzyme of interest was present in the supernatant, and the supernatant was used for the next purification.

Step 2

By using a Q-Sepharose HP 16/20 anion exchange column equilibrated in advance with the same 20 mM Tris-HCl buffer (pH 8.5) as used for the enzyme solution, separation was carried out with a sodium chloride gradient, whereby a fraction containing the enzyme of interest was obtained.

Step 3

By using a Phenyl-Sepharose HP 16/20 hydrophobic column equilibrated in advance with a 20 mM Tris-HCl buffer (pH 8.5) containing 2 M ammonium sulfate, separation was carried out with an ammonium sulfate gradient, whereby a fraction containing the enzyme of interest was obtained.

Step 4

After desalting, by using a Mono Q anion exchange column equilibrated in advance with a 20 mM Tris-HCl buffer (pH 7.5), separation was carried out with a sodium chloride gradient, whereby a fraction containing the enzyme of interest was obtained.

By the purification described above, as shown in Table 1, the enzyme is purified to about 6-fold and a purified preparation can be obtained at a yield of about 12%.

<Method for Measuring Enzymatic Activity>

A reaction solution having a composition of 50 μl of an enzyme solution, 50 μl of 0.05 M L-rhamnose, 50 μl of 0.01 M manganese chloride and 0.05 M glycine-NaOH buffer (pH 9.0) was used. The reaction was carried out at a reaction temperature of 50° C. for 10 minutes. The produced L-rhamnulose was measured by the cysteine-carbazole method, and the amount of enzyme that produces 1 μmol of L-rhamnulose per minute was determined to be 1 unit (U).

TABLE 1

| Purification step | Total activity (U) | Specific activity (U/mg) | Purification fold | Yield (%) |
|---|---|---|---|---|
| Crude enzyme (step 1) | 40 | 0.24 | 1.0 | 100 |
| Q-Sepharose (step 2) | 20 | 0.6 | 2.5 | 50 |
| Phenyl Toyopearl (step 3) | 13 | 1.3 | 5.4 | 33 |
| Mono Q (step 4) | 4.3 | 1.4 | 5.8 | 11.5 |

EXAMPLE 2

Object: L-rhamnose isomerase derived from *Pseudomonas stutzeri* is an enzyme catalyzing an isomerization reaction between L-rhamnose and L-rhamnulose, and it has been already known that it also catalyzes an isomerization reaction between D-psicose and D-allose. In this study, with the aim of obtaining a novel enzyme which has a higher reaction efficiency between D-psicose and D-allose and is excellent in thermal stability, various properties of L-rhamnose isomerase derived from *Bacillus pallidus* were examined.

(1) Molecular Weight

The molecular weight of a monomer is about 45,000, and it is a tetramer composed of 4 subunits and having a molecular weight of about 180,000.

Method for determining molecular weight: As for the molecular weight of the enzyme, a molecular weight assay was carried out using high performance liquid chromatography. The determination conditions were as follows. AKTA system manufactured by Amersham was used as an apparatus, and Superdex 200 pg 16/60 was used as a column, and the flow rate was 1 ml/min and a 0.3 M aqueous solution of sodium chloride was used as a solvent. As for standard molecular weight markers, bovine catalase (molecular weight: 240000), rabbit aldolase (molecular weight: 160000), bovine serum albumin (molecular weight: 67000) and egg albumin (molecular weight: 45000) were used as standard substances, and the molecular weight thereof was determined to be about 180,000 based on the elution position.

As for the molecular weight of the monomer which is a subunit, the molecular weight was determined based on the position of the band in SDS-PAGE and the mobility of the standard substances and found to be about 45,000.

Based on these results, it was found that this enzyme has a molecular weight of about 180,000 and is composed of 4 subunits, each of which has a molecular weight of about 45,000.

(2) Enzymological Properties

The measurement methods and evaluation of the shown technical results and the like will be described.

The optimal pH of L-rhamnose isomerase derived from *Bacillus pallidus* was examined. The results are shown in FIG. 1A. With the use of the purified enzyme, a reaction was carried out at 50° C. using L-rhamnose as a substrate at each pH value. The highest activity exhibited at pH 6 was assumed to be 100%, and the relative activities are shown for the respective pH values. The pH at which the highest activity was exhibited was pH 6 in a phosphate buffer. The activity was exhibited in a wide range of from pH 6 to pH 9.

The optimal pH of L-rhamnose isomerase derived from *P. stutzeri* was examined. The results are shown in FIG. 1B. The reaction was carried out in the same enzymatic reaction conditions as in FIG. 1A at each pH value, and the highest activity exhibited at pH 9 in a glycine-NaOH buffer was assumed to be 100%, and the relative activities are shown. The pH at which the highest activity was exhibited was pH 9 in a glycine-NaOH buffer. With regard to the activity thereof, the optimal pH was present in a range of from pH 7 to around pH 9.

The stable pH of L-rhamnose isomerase derived from *Bacillus pallidus* was examined. The results are shown in FIG. 2A. The purified enzyme was kept at 4° C. for 1 hour at each pH value, and the remaining activity was measured. The remaining activity at pH 7 was assumed to be 100%, and the relative activities are shown. As shown by these results, this enzyme was stable within a wide range of from pH 6 to pH 9.

The stable pH of L-rhamnose isomerase derived from *P. stutzeri* was examined. The results are shown in FIG. 2B. The test conditions are the same as in FIG. 2A. It is apparent that the stable pH range of this enzyme is from 7 to 9.

(3) "L-rhamnose isomerase" of the protein having an L-rhamnose activity derived from *Bacillus pallidus* strain 14a (IPOD FERM BP-10407), and L-rhamnose isomerase produced by *Pseudomonas stutzeri* LL172 (IPOD FERM BP-08593) are compared.

The method for measuring the substrate specificity (relative activity (%)) will be described.

A reaction solution having a composition of 50 μl of the purified enzyme solution, 50 μl of 0.05 M of each substrate sugar, 50 μl of 0.01 M manganese chloride and 0.05 M glycine-NaOH buffer (pH 9.0) was used. The reaction was carried out at a reaction temperature of 50° C. for 10 minutes. The produced ketose corresponding to the respective substrates was measured by the cysteine-carbazole method, and the activity that produces 1 μmol of the ketose per minute was measured for the respective substrates.

As shown in Table 2, the relative activities (%) thereof against L-lyxose, L-mannose and D-allose are 23.9% (43.9% in the case of the L-rhamnose isomerase produced by LL172), 11% (33.4% in the case of the L-rhamnose isomerase produced by LL172) and 5.5% (7.2% in the case of the L-rhamnose isomerase produced by LL172), respectively, when the enzymatic activity thereof against L-rhamnose is assumed to be 100%, and it has substantially the same substrate specificity.

As described above, "L-rhamnose isomerase" of the protein having an L-rhamnose activity derived from *Bacillus pallidus* strain 14a (IPOD FERM BP-10407) has been confirmed to have at least activities of (L-xylulose→) L-lyxose, (L-fructose), L-mannose, (D-xylulose→) D-lyxose. This indicates that the respective rare sugars can be produced. However, the production of any of the rare sugars with a thermotolerant enzyme has not been reported yet.

Therefore, the present invention can provide a method for producing a variety of rare sugars, characterized by utilizing an ability of isomerization with a wide range of specificity of said protein having an L-rhamnose isomerase activity compared with those derived from *Pseudomonas stutzeri*.

TABLE 2

| Substrate | Enzyme derived from *B. Pallidus* (relative activity %) | Enzyme derived from *P stutzeri* (relative activity %) |
| --- | --- | --- |
| L-rhamnose | 100 | 100 |
| L-lyxose | 23.9 | 43.7 |
| L-mannose | 11.0 | 33.4 |
| D-allose | 5.6 | 7.2 |
| D-lyxose | 0.14 | 0.006 |

(a) A temperature at which the enzymatic activity thereof is the highest (optimal temperature) is 80° C. in a reaction time of 10 minutes, which is higher by 20° C. compared with 60° C. in the case of the enzyme derived from LL172, and it is stable up to 50° C. in the case of a heat treatment condition of 1 hour in terms of the effect of temperature on the enzymatic activity thereof, which is also higher by 10° C. compared with 40° C. in the case of the enzyme derived from LL172.

(b) A pH at which the enzymatic activity thereof is the highest (optimal pH) ranges from 6 to 9, and it has a characteristic that the activity thereof is high even in an acidic region compared with the enzyme derived from LL172, which has an optimal pH of from 8 to 9, and it is stable within a pH range of from 6 to 9 in terms of the effect of pH on the enzymatic activity thereof, and has a characteristic that it is stable even in an acidic region compared with the enzyme derived from LL172, which is stable within a pH range of from 7 to 9.

EXAMPLE 3

Production of D-allose using L-rhaminose isomerase produced by *Bacillus pallidus* strain 14a (IPOD FERM BP-10407)

The Production of D-allose from D-psicose is carried out as follows. By using L-rhamnose isomerase produced by L-rhamnose isomerase produced by *Bacillus pallidus* strain 14a (IPOD FERM BP-10407), an immobilized enzyme is prepared by a crosslinking method with glutaraldehyde. Then, about 20000 units of immobilized enzyme is added to 100 ml of a 50% D-psicose solution (obtained by dissolving D-psicose in a glycine buffer (p9) containing 1 mM $MnCl_2$) to allow a reaction to proceed at 60°C., whereby an enzymatic reaction solution is obtained. This reaction solution contains D-psicose and D-allose at final concentrations of 35% and 15%, respectively.

In this way, in the case where D-allose is produced by an enzymatic reaction using 50% D-psicose as a raw material, the product can be obtained as a mixed solution of 35% D-psicose and 15% D-allose.

From this enzymatic reaction product, D-psicose and D-allose are rapidly separated, and high-purity D-allose is obtained.

Example of Separation Procedure (1) Ethanol of high purity (99%) is sufficiently cooled in advance. Since the concentration of a sugar should be 50% or more, a bioreactor with which D-allose is produced from D-psicose is checked in advance.

(2) A 1-L beaker is placed at the outlet of the bioreactor, and 500 ml of cooled 99% ethanol is added to the beaker in advance and stirred in ice.

(3) The resulting solution produced in the bioreactor is directly added dropwise to the cooled ethanol, and the mixture is thoroughly stirred, whereby a precipitate is formed.

(4) When the final concentration of ethanol becomes 60% or less, the precipitate is dissolved, therefore, in order to promote the crystallization, one piece of seed crystal of D-allose is added to the cooled ethanol. The ethanol solution is exchanged for a fresh ethanol solution in a condition that the final concentration of ethanol is not lower than 50%.

(5) The mixed solution of ethanol and a sugar liquid after completion of the operation is left at 4° C. overnight. The formed sugar crystal is collected by filtration through a 3G1 glass filter, washed several times with 99% ethanol and dried under reduced pressure to completely remove ethanol.

(6) The purity of the obtained sugar crystal is analyzed by HPLC, and a crystal of D-allose of a purity of 99% or more can be obtained. In the filtrate after filtration, D-psicose is contained, therefore, ethanol is removed and the resulting solution is concentrated. Then, the concentrate is reused in the bioreactor.

At the same time of separation of D-allose, desalting, deionization, concentration and crystallization can be carried out, therefore, the separation methods, all of which have been carried out in separate steps, can be integrated into one step. Accordingly, it is possible to treat a large amount in a short time.

Thus, the application thereof as a production method of a rare sugar D-allose is large.

INDUSTRIAL APPLICABILITY

Since the gene sequence has been identified, it becomes possible to perform a variety of experiments by a molecular biological technique utilizing this gene sequence.

For example, it is possible to perform mass production by transforming *E. coli* with this gene. Alternatively, for example, by further ligating any new gene to this gene, it is possible to produce an enzyme having a new property.

For the production of a new material by expanding a monosaccharide, it is most useful to perform the production using a bioreactor in general. For example, in the case where D-fructose with high sweetness is produced by an isomerization reaction from D-glucose with low sweetness, a bioreactor is constructed by immobilizing D-xylose isomerase and used. Also in this industrial production, by utilizing a thermotolerant D-xylose isomerase, it has become possible to construct a stable bioreactor, which has been used.

The thermotolerant L-rhamnose isomerase obtained this time was found to be an enzyme having heat resistance in that the optimal temperature is higher by about 20° C. than that of L-rhamnose isomerase which has been reported so far. Further, L-rhamnose isomerase produced by *E. coli* hardly exhibits an activity against D-allose, however, L-rhamnose isomerases produced by *Bacillus pallidus* strain 14a obtained in the present invention has an extremely advantageous property to exhibit an activity against D-allose as well as having heat resistance.

By using this enzyme, it became possible to produce D-allose and other rare sugars more efficiently than the production method of D-allose using *Pseudomonas stutzeri* LL172a which had been discovered and reported by us before.

This enzyme is not only excellent in heat resistance, but also exhibits its activity in a wide pH range and is stable in a wide pH range. This indicates that the enzyme can respond to the change in pH in the production of a rare sugar in a bioreactor, therefore, it is further advantageous in the industrial production of a rare sugar.

BRIEF DESCRIPTION OF THE DRAWINGS

[FIG. 1A] FIG. 1A shows the optimal pH of L-rhamnose isomerase derived from *B. steanthermophilus*.

[FIG. 1B] FIG. 1B shows the optimal pH of L-rhamnose isomerase derived from *P. stutzeri*.

[FIG. 2A] FIG. 2A shows the stable pH of L-rhamnose isomerase derived from *B. steanthermophilus*.

[FIG. 2B] FIG. 2B shows the stable pH of L-rhamnose isomerase derived from *P. stutzeri*.

[FIG. 3A] FIG. 3A shows the optimal reaction temperatures of L-rhamnose isomerases derived from *B. steanthermophilus* and *P. stutzeri*.

[FIG. 3B] FIG. 3B shows the temperature stabilities of L-rhamnose isomerases derived from *B. steanthermophilus* and *P. stutzeri*.

FIG. 4 is a view showing the base sequence of a gene (DNA) encoding a protein having an L-rhamnose isomerase activity derived from *Pseudomonas stutzeri* LL172 (FERM BP-08593) and the amino acid sequence thereof. The upper sequence is SEQ ID NO: 3. The lower sequence is SEQ ID NO: 4.

FIG. 5 is a view showing the comparison of the amino acid sequences of L-rhamnose isomerase derived from *Pseudomonas stutzeri* LL172 strain (FERM BP-08593) and L-rhamnose isomerase derived from a known Bacillus subtilis. The upper sequence is SEQ ID NO: 4. The lower sequence is SEQ ID NO: 5.

FIG. 6 is a view illustrating the homology of L-rhamnose isomerase derived from *Pseudomonas stutzeri* LL172 strain (FERM BP-08593) to an unidentified putative isomerase derived from a known Streptmyces coelicolor or Thermotoga maritima. The upper sequence is SEQ ID NO: 4. The middle sequence is SEQ ID NO: 6. The lower sequence is SEQ ID NO: 7.

[FIG. 7] FIG. 7 shows isomerization reactions of hexoses catalyzed by L-rhamnose isomerase shown by using Izumoring. The thick black lines indicate the isomerization reactions which were confirmed to be catalyzed. The thick dotted lines indicate the isomerization reactions in which a catalytic reaction was not confirmed.

[FIG. 8] FIG. 8 shows isomerization reactions of pentoses catalyzed by L-rhamnose isomerase shown by using Izumoring. The thick black lines indicate the isomerization reactions which were confirmed to be catalyzed. All the isomerization reactions were confirmed.

[FIG. 9] FIG. 9 shows isomerization reactions of hetetroses catalyzed by L-rhamnose isomerase shown by using Izumoring. The thick black lines indicate the isomerization reactions which were confirmed to be catalyzed. All the isomerization reactions were confirmed.

The invention claimed is:

1. An isolated protein, comprising:
   the amino acid sequence of SEQ ID NO: 2 and having L-rhamnose isomerase activity.

2. The isolated protein according to claim 1, wherein the relative percentages of the enzymatic activities of said isolated protein against L-lyxose, L-mannose and D-allose are 23.9%, 11% and 5.5%, respectively, when the enzymatic activity of said isolated protein against L-rhamnose is 100%.

3. The isolated protein according to claim 1, wherein said isolated protein has an optimal activity and stability in the pH range 6-9, and wherein optimal enzymatic activity of said isolated protein is the highest at 80° C. in a reaction time of 10 minutes and the isolated protein is stable up to one hour at 50° C. in a solution containing 0.01 M manganese chloride and 0.5 M glycine-NaOH buffer, pH 9.0.

4. A fusion protein, comprising:
   the isolated protein according to claim 1.

5. A method for producing D-allose, comprising:
   converting D-psicose to D-allose by the isomerization activity of said isolated protein of claim 1, and
   incubating said D-psicose and said isolated protein at a temperature of 35 to 80° C. in a solution containing 0.01 M manganese chloride and 0.5 M glycine-NaOH buffer, pH 9.0.

* * * * *